United States Patent
May et al.

(10) Patent No.: US 8,620,588 B2
(45) Date of Patent: Dec. 31, 2013

(54) METHOD, SYSTEM, AND COMPUTER PROGRAM PRODUCT FOR DETERMINING A PUTATIVE AMINO ACID SEQUENCE

(75) Inventors: Michael May, Cheshire (GB); Jing Wen Yao, Cambridgeshire (GB)

(73) Assignee: Shimadzu Research Laboratory (Europe) Limited, Manchester, Lancashire (GB)

( * ) Notice: Subject to any disclaimer, the term of this patent is extended or adjusted under 35 U.S.C. 154(b) by 593 days.

(21) Appl. No.: 10/515,955

(22) PCT Filed: May 30, 2003

(86) PCT No.: PCT/GB03/02353
§ 371 (c)(1),
(2), (4) Date: Nov. 29, 2004

(87) PCT Pub. No.: WO03/102572
PCT Pub. Date: Dec. 11, 2003

(65) Prior Publication Data
US 2006/0172365 A1 Aug. 3, 2006

(30) Foreign Application Priority Data
May 30, 2002 (GB) .................................. 0212470.9

(51) Int. Cl.
*G01N 33/48* (2006.01)
(52) U.S. Cl.
USPC .......................................................... 702/19
(58) Field of Classification Search
None
See application file for complete search history.

(56) References Cited

U.S. PATENT DOCUMENTS

| 5,470,753 A * | 11/1995 | Sepetov et al. .................... 506/6 |
| 2002/0102610 A1 * | 8/2002 | Townsend et al. ............. 435/7.1 |
| 2002/0168682 A1 | 11/2002 | Goodlett ........................ 435/7.1 |

FOREIGN PATENT DOCUMENTS

| EP | 1130399 | 9/2001 |
| WO | 02/08767 | 1/2002 |
| WO | 02/21139 | 3/2002 |

OTHER PUBLICATIONS

Dancik et al., Journal of Computational Biology, 1999, vol. 6, No. 3/4, p. 327-342.*
Papayanopoulos et al., Mass Spectrometry Reviews, 1995, 14, 49-73.*
Horn et al., Proc Natl Aced Sci, 2000, vol. 97, No. 19, p. 10313-10317.*
Schlosser et al., Proteomics, Apr. 2002, vol. 2, Issue 5, p. 524-533.*
Scoble et al., Fresenius Z. Anal. Chem., 1987, col. 327, p. 239-245.*
Sakurai et al., Biomedical Mass Spectrometry, 1984, vol. 11, No. 8, p. 396-399.*
Johnson et al., Biomedical and Environmental Mass Spectrometry, 1989, vol. 18, 945-957.*
Mann et al. (Anal. Chem. 1994,66, 4390-4399).*
Zhang et al. (Anal. Chem., 2000, 72, 2482-2489).*
Mass Spectrometry Reviews—vol. 14, 1995, XP001051562, The Interpretation of Collision-Induced Dissociation Tandem Mass Spectra of Peptides by Ioannis A. Papayannopoulos, pp. 49-73.

* cited by examiner

*Primary Examiner* — Pablo S Whaley
(74) *Attorney, Agent, or Firm* — Jacobson Holman PLLC

(57) ABSTRACT

The present invention is concerned with methods for the de novo sequencing of polypeptides from data obtained from mass spectrometry devices, particularly from (MS)n devices.

21 Claims, 14 Drawing Sheets

Figure 3

| A | B | C | D | E | F | G | H | I | J | K | L | M |
|---|---|---|---|---|---|---|---|---|---|---|---|---|
| Gly | C2H3NO | 57.02146 | 57.052 | 1 | H— | — | 30 | W | A | 810 | 5.97 | |
| Ala | C3H5NO | 71.03711 | 71.079 | 15 | CH3— | — | 44 | W | A | 610 | 6.00 | |
| Ser | C3H5NO2 | 87.03203 | 87.078 | 31 | HO-CH2— | 18 (H2O) | 60 | — | U | 420 | 5.68 | |
| Pro | C5H7NO | 97.05276 | 97.116 | — | (pyrrolidine ring) | — | 70 | V | A | -170 | 6.30 | |
| Val | C5H9NO | 99.06841 | 99.132 | 43 | (H3C)2CH— | — | 72 | W | A | -750 | 5.96 | |
| Thr | C4H7NO2 | 101.04768 | 101.104 | 45 | CH3CH(OH)— | 18 (H2O) | 74 | — | U | 290 | 6.16 | |
| Cys | C3H5NOS | 103.00918 | 103.145 | 47 | HS-CH2— | 34 (H2S) | 76 | S | U | 360 | 5.07 | |
| Ile | C6H11NO | 113.08406 | 113.159 | 57 | CH3CH2CH(CH3)— | — | 86(72) | — | A | -1450 | 6.02 | |
| Leu | C6H11NO | 113.08406 | 113.159 | 57 | (H3C)2CHCH2— | — | 86(72) | S | A | -1650 | 5.98 | |
| Asn | C4H6N2O2 | 114.04293 | 114.103 | 58 | H2NCOCH2— | 17 (NH3) | 87(70) | — | U | 890 | 5.41 | |
| Asp | C4H5NO3 | 115.02694 | 115.088 | 59 | ⊖HOOCCH2— | — | 88 | — | C | 610 | 2.77 | |
| Gln | C5H8N2O2 | 128.05858 | 128.130 | 72 | H2NCOCH2CH2— | 17 (NH3) | 101(129,84) | — | U | 970 | 5.65 | |
| Lys | C6H12N2O | 128.09496 | 128.174 | 72 | ⊕H3NCH2CH2CH2CH2— | 17 (NH3) | 101(129,112,84,70) | — | C | 460 | 9.74 | |
| Glu | C5H7NO3 | 129.04259 | 129.114 | 73 | ⊖HOOCCH2CH2— | 18? (H2O?) | 102(84) | — | C | 510 | 3.22 | |
| Met | C5H9NOS | 131.04048 | 131.198 | 75 | CH3-S-CH2CH2— | 48 (CH3SH) | 104(61) | W | A | -660 | 5.74 | |
| His | C6H7N3O | 137.05891 | 137.141 | 81 | (imidazole-CH2—) | — | 110 (166,138,123,121,82) | — | C | 690 | 7.59 | |
| Phe | C9H9NO | 147.06841 | 147.176 | 91 | C6H5-CH2— | — | 120(91) | V | A | -1520 | 5.48 | |
| Arg | C6H12N4O | 156.10111 | 156.188 | 100 | H2N-C(=NH2+)-NH-CH2CH2CH2— | 17 (NH3) | 129 (112,100,98,87,73,70,59) | — | C | 690 | 10.76 | |
| Tyr | C9H9NO2 | 163.06333 | 163.175 | 107 | HO-C6H4-CH2— | 18? (H2O?) | 136 | V | U | -1430 | 5.66 | |
| Trp | C11H10N2O | 186.07931 | 186.213 | 130 | (indole-CH2—) | — | 159 | V | A | -1200 | 5.89 | |

Figure 4
(A) 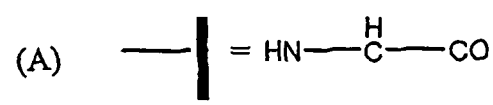
(B) 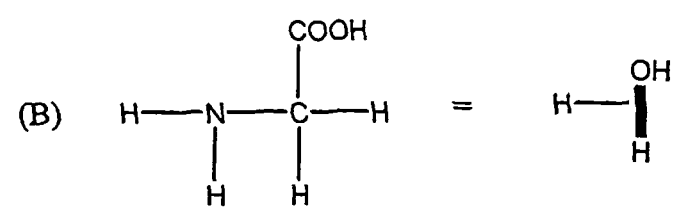
(C) 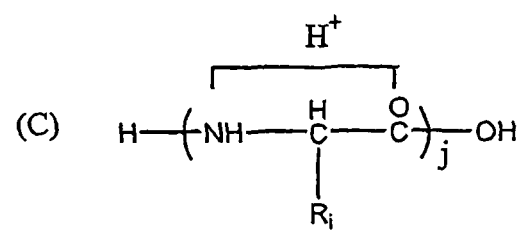
(D) 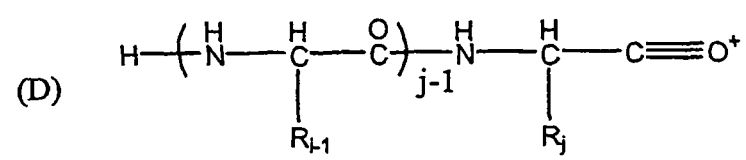

Figure 5
(A) 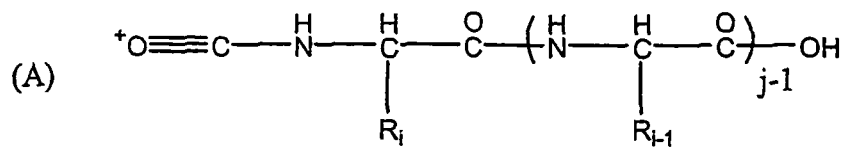
(B) 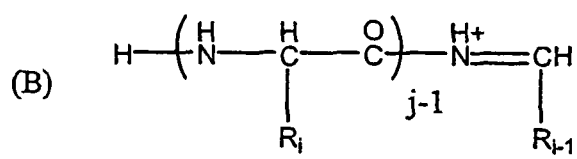
(C) 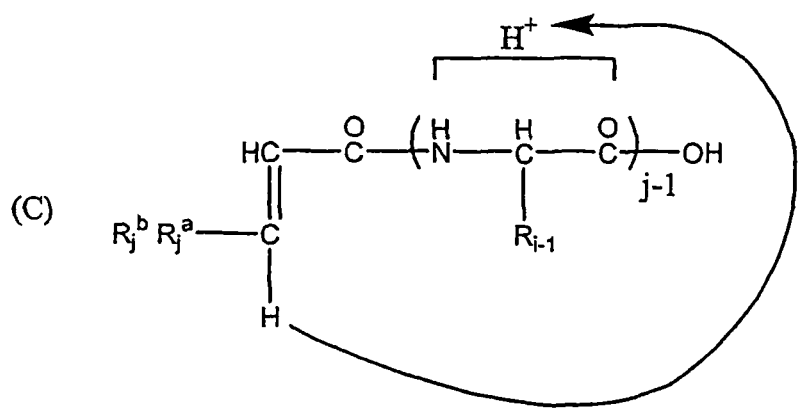
(D) 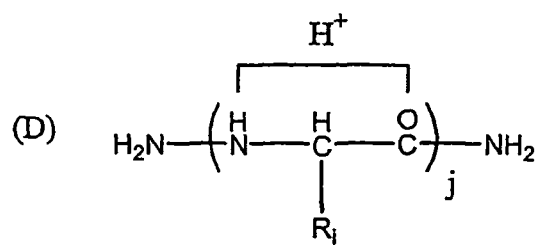

Figure 7

| Series2 / Series1 | b y | b $\bar{y}$ | $\bar{b}$ y | $\bar{b}$ $\bar{y}$ |
|---|---|---|---|---|
| b y | n | 1y,2b | 1b,2y | n |
| b $\bar{y}$ | 1b,2y | n | 1b,2y | 1b,2y |
| $\bar{b}$ y | 1y,2b | 1y,2b | n | 1y,2b |
| $\bar{b}$ $\bar{y}$ | n | 1y,2b | 1b,2y | n |

SEQUENCE LISTING

```
<160> NUMBER OF SEQ ID NOS: 16

<210> SEQ ID NO 1
<211> LENGTH: 8
<212> TYPE: PRT
<213> ORGANISM: Artificial Sequence
<220> FEATURE:
<223> OTHER INFORMATION: Example synthetic sequence

<400> SEQUENCE: 1

Arg Glu Gly Gly Ala Ile Phe Glu
 1               5

<210> SEQ ID NO 2
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 2

Glu Gly Gly Ala Ile Phe Glu
 1               5

<210> SEQ ID NO 3
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 3

Phe Ile Ala Gly Gly Glu Arg
 1               5

<210> SEQ ID NO 4
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 4

Leu Tyr Leu Lys Gly Glu Arg
 1               5

<210> SEQ ID NO 5
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 5

Tyr Glu Leu Gln Asp Pro Arg
 1               5

<210> SEQ ID NO 6
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 6

Ile Val Leu Asp Gly Leu Tyr
```

-continued

```
<210> SEQ ID NO 7
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 7

Arg Ala Leu Pro Pro Leu Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 8

Arg Gly Tyr Glu Val Val Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 9

Ile Trp Ile Asp Gly Val Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 10

Met Glu Gly Asn Asp Leu Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 11

Leu Gly Glu Leu Asp Gly Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 12

His Tyr Ala Arg Gly Val Arg
1               5
```

```
<210> SEQ ID NO 13
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 13

Ile Glu Gly Ile Thr Ala Arg
 1               5

<210> SEQ ID NO 14
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 14

Asn Trp Ala Arg Gly Val Arg
 1               5

<210> SEQ ID NO 15
<211> LENGTH: 7
<212> TYPE: PRT
<213> ORGANISM: Artificial Sequence
<220> FEATURE:
<223> OTHER INFORMATION: Example synthetic sequence

<400> SEQUENCE: 15

Asn Ala Asp Ile Asn Arg Arg
 1               5

<210> SEQ ID NO 16
<211> LENGTH: 8
<212> TYPE: PRT
<213> ORGANISM: Artificial Sequence
<220> FEATURE:
<223> OTHER INFORMATION: Example synthetic sequence

<400> SEQUENCE: 16

Glu Phe Ile Ala Gly Gly Glu Arg
 1               5
```

METHOD, SYSTEM, AND COMPUTER PROGRAM PRODUCT FOR DETERMINING A PUTATIVE AMINO ACID SEQUENCE

This is a nationalization of PCT/GB03/02353 filed May 30, 2003 and published in English.

The present invention is concerned with methods for the de novo sequencing of polypeptides from data obtained from mass spectrometry devices, particularly from $(MS)^n$ devices.

It is currently well known in the art to use mass spectrometry to confirm the identity of a sample protein/polypeptide (the two terms are interchangeable herein unless stated otherwise). Protein mass fingerprinting programs such as MASCOT (based on the MOWSE algorithm) use mass spectrometry data generated from the enzymatic digestion (using e.g. Trypsin) of a protein to attempt to identify it from primary sequence databases (Matrix Science Ltd, GB; Perkins et al., Electrophoresis. 1999 December;20(18):3551-67; PMID: 10612281). In the prior art approaches to identifying proteins from mass spectrometry data, the experimental data are peptide molecular weights (in the form of mass to charge ratios) from the digestion of a protein by an enzyme. Other approaches use tandem mass spectrometry data from one or more peptides (also known as MS/MS and $MS^2$), an ion species of interest being selected and fragmented to give hierarchical product ion spectra. Still others combine mass data with amino acid sequence data.

Notably, these techniques do not actually derive a polypeptide sequence from the MS or MS/MS data and instead provide a score or probability by which the mass spectrometry data is compared to the (already known) sequences on databases, and an experimenter can select the preferred database sequence (i.e. the one with the best score or highest probability) as being a likely candidate for the protein being analyzed.

However, these prior art methods are unable to directly use data produced by the most recently developed mass spectrometry methods, namely multiple tandem mass spectrometry ($(MS)^n$, tandem in time/space) since it results in the generation of extremely large volumes of hierarchical product ion data which is too complex to be compared to the databases. Furthermore, the prior art methods are incapable of directly deriving actual sequence data from mass spectrometry data, particularly from the highly complex $(MS)^n$ spectra. Current $(MS)^n$ devices include MS/MS (tandem, i.e. n=2) mass spectrometers, as well as devices such as the Kratos Axima QIT TOF mass spectrometer.

Papayannopoulos, IA ("The interpretation of collision-induced dissociation tandem mass spectra of peptides", Mass Spectrom. Rev., 1995, 14(1) 49-73) discusses the interpretation of MS/MS tandem mass spectra of peptides, and computer-program based solutions. However, the methodology taught in the paper is an extremely subjective one, is applicable only to small peptides (maximum size of about 20 amino acids), and provides no specific teaching of how a given set of data should be interpreted to give a candidate amino acid sequence(s). At Section "VII. Conclusions" it concludes that "Furthermore, continuing improvements in mass spectrometric instrumentation make it possible to acquire tandem CID mass spectral data of larger and larger peptides and small proteins; although at present such data appear to be of limited practical utility, . . . " and that " . . . although the correct interpretation of tandem CID mass spectra of peptides of unknown structure can sometimes be difficult . . . using MS/MS data to confirm the expected sequence of peptides, or to identify modifications in otherwise known sequences, is within the reach of anyone seriously interested in the application of tandem mass spectrometry . . . "

In addition, there are a number of errors in the Papayannopoulos paper (above) meaning that if followed, incorrect masses will be calculated for various daughter, displacement and neutral loss ions, and/or that m/z peaks will be incorrectly attributed to ion species in a spectrum.

Thus a person following the teaching of Papayannopoulos would not achieve the results of the present invention, as detailed below. It should also be noted that the teaching of Papayannopoulos is only concerned with MS/MS (i.e. $MS^2$) spectra, and not $MS^n$ spectra where n>2.

The present invention seeks to overcome the prior art disadvantages and provides for a significant and substantial advance in the field of protein sequencing According to the present invention there is provided a method for determining at least one putative (i.e. candidate) amino acid sequence for a sample polypeptide, said sample polypeptide being partially degraded, said method comprising the steps of:

(i) obtaining a soft ionization mass spectrum of said partially degraded sample polypeptide giving a set of m/z peaks of ion species obtained from said partially degraded sample polypeptide;

(ii) with said set of m/z peaks obtained in step (i), determining a plurality of candidate m/z peak sets, each m/z peak in each candidate m/z peak set differing from its at least one neighbor by the mass of an amino acid;

(iii) with each candidate m/z peak set determined at step (ii), determining a sequence of mass differences between each m/z peak and its at least one neighbor and discarding any candidate m/z peak sets whose mass difference sequence in reverse order does not form at least part of the mass difference sequence of another of said candidate m/z peak sets;

(iv) identifying any Difference Sets in the remaining m/z peak sets;

(v) with the remaining candidate m/z peak sets, identifying and discarding any candidate m/z peak set which is a contiguous subsequence of another candidate m/z peak set; and (vi) determining a putative amino acid sequence for each remaining candidate m/z peak set, each amino acid sequence being that of the amino acids which correspond to the mass differences between each m/z peak and its at least one neighbour, each putative amino acid sequence comprising at least partial putative amino acid sequence of said sample polypeptide.

By the "at least one neighbour" of an m/z peak is meant the closest m/z value above and/or below the m/z peak value. So, for example, in a nominal set of m/z peaks having values 375, 300, 347, 372 and 331, the peak value 331 has two neighbors, namely 300 and 347.

The sample polypeptide mass can be at least 3000 Da, for example at least 4000, 5000, 6000, 7000, 8000, 9000, 10000 or 15000 Da. The partial degradation of the sample polypeptide can result in fragments having masses of up to e.g. 3000 or 4000 Da.

The soft ionisation mass spectrum can give at least 3 m/z peaks, for example at least 4, 5, 6, 7, 8, 9, 10, 15, 20, 25, 30, 40, 50, 75 or 100 m/z peaks.

Each candidate m/z peak set can comprise at least 3 m/z peaks, for example at least 4, 5, 6, 7, 8, 9, 10, 15, 20, 25, 30, 40 or 50 m/z peaks.

The present invention allows the production of candidate amino acid sequences from mass spectra which, to date, have been considered uninterpretable. This is achieved by the use of reverse sequences at step (iii), which has not previously been suggested. The generation of all possible candidate mass peak sets which could correspond to m/z peaks obtained from a sample polypeptide also helps ensure that all possible candidate sequences are considered. Together with the use of inductive and/or deductive processes to identify Difference Sets, the present invention is able to achieve de novo sequencing of a sample polypeptide, a significant advantage over the prior art.

Soft ionisation techniques are well known in the art and, generally speaking, result in minimal fragmentation of the sample being ionised, and typically work well with polar and thermally labile compounds. Examples of soft ionisation techniques include (but are not limited to) matrix-assisted laser desorption and ionisation (MALDI), electrospray ionisation (EI), atmospheric pressure chemical ionisation (APCI), fast atom bombardment (FAB) and chemical ionisation (CI) etc. In particular MALDI-time of flight (MALDI-TOF) mass spectrometry can be used in the present invention.

Examples of matrix molecules which can be used with MALDI include: 2-amino-4-methyl-5-nitropyridine, 2-amino-5-nitropyridine, 6-aza-2-thiothymine, caffeic acid, α-cyano-4-hydroxy cinnamic acid (ACH), 2,5-dihydroxybenzoic acid (gentisic acid, DHB), 2,5-dihydroxybenzoic acid and fucose (1:1), ferulic acid, glycerol with rhodamine 6G (0.1M), 2-(4-hydroxyphenylazo) benzoic acid (HABA), 3-hydroxypicolinic acid (HPA), nicotinic acid, 3-nitrobenzyl alcohol, 3-nitrobenzyl alcohol with rhodamine 6G, 3-nitrobenzyl alcohol with 1,4-diphenyl-1,3-butadien (0.1M), 2-pyrazinecarboxylic acid, 3,5-dimethoxy-4-hydroxy cinnamic acid (sinapinic acid, SA), and succinic acid, and a skilled person will be readily able to determine exactly which matrix molecules can be used with a given sample polypeptide. Other matrix molecules which my be used include 5-chloro-2-hydroxybenzoic acid (5-chlorosalycylic acid, CSA), trans-indole-acrylic acid (IAA), 5-methoxysalicylic acid (5-methoxy-2-hydroxybenzoic acid, MSA), norharmane (9H-pyrido[3,4-b]indole, nH), picolinic acid (2-pyridineboxylic acid, PA), 2,4,6-trihydroxy-acetophenone (THAP), and 1,8,9-trihrdroxy-anthracene (dithranol), and cobalt ultra fine metal powder.

Although peptide ions typically fragment at the peptide backbone to produce series of fragment ions (for example as a result of internal energy derived in the ionisation process), this can be supplemented by e.g. colliding the sample polypeptide ions with neutral gas molecules (i.e. by employing collision-induced decomposition in electrospray mass spectrometry). In MALDI spectrometry, the fragmentation of a protein/peptide into ions can result not only from initial ionisation, but also by other events such as post source decay (PSD) which can be obtained along the trajectory of ions along the time of flight (TOF) mass spectrometer.

The ionisation of proteins results in the generation of a number of ion species as a result of the structure of the protein (see FIG. 1). For example, the cleavage of a CH—CO bond results in the generation of a- and x-daughter ions. The a-ions are N-terminal fragments and the x-ions are C-terminal fragments. Similarly, the cleavage of a backbone CO—NH bond results in the generation of N-terminal b- and C-terminal y-daughter ions. The cleavage of an NH—CH bond results in the generation of N-terminal c- and C-terminal z-daughter ions. The most frequently generated ion species are the b- and y-daughter ions together with a-daughter ions.

It is also possible for End Ion Clusters to be generated from each of the different daughter ion species. Each of the N-terminal ion species (i.e. the a-, b- and c-daughter ions) can produce hybrid ions at a mass of the daughter ion minus the mass of the terminal $NH_2$ group (16 Daltons).

In addition, a-ions can be protonated, giving a hybrid peak at the daughter ion mass +1 Dalton. Other hybrid peaks can also arise at the daughter ion mass −2 Daltons and +1 Dalton corresponding, respectively, to $y_n-2$ and $z_n+1$ ions.

In an example sequence $NH_2$—$CHR_1$—CO—NH—$CHR_2$—CO—NH—$CHR_3$—COOH an abc cluster (i.e. c-ion is 17 Daltons heavier than a b-ion which in turn is 28 Daltons heavier than an a-ion) can be generated by each CHR—CO—NH, as can a corresponding xyz cluster. Ions and clusters of ions from adjacent amino acids in the protein are separated by the mass of the amino acid.

These various daughter ions and end ion clusters are generally referred to herein as defining "Difference Ions" and "Difference Sets" and they can be identified in the candidate m/z peak sets in a number of ways. Difference Sets include Displacement Sets, which can identify ion series (e.g a-, b-, c-, x-, y-, and z-), and Neutral Loss Sets, which can provide information about amino acids.

The present invention, with its various filtering and identification steps, is able to identify all the potential amino acid sequences which could result in a given set of m/z peaks, and remove those amino acid sequences which are incorrect or which are contiguous subsequences of a larger set (sequence), to produce a final result of at least one putative amino acid sequence. For some amino acid sequences, the final result may just be a single putative amino acid sequence, whereas for other (particularly, larger) amino acid sequences it may produce more than one putative amino acid sequence, corresponding to fragments of the original sample polypeptide, or which may result from there being more than one possible solution to a particular set of m/z peaks.

Importantly, the present invention creates de novo putative amino acid sequences, and does not rely upon the sample polypeptide and its corresponding set of m/z peaks being in a database and being correlated with an m/z peak set generated by mass spectrometry of the sample polypeptide.

The sample polypeptide can be partially degraded using an enzyme selected from the group consisting of exopeptidases and endopeptidases. These are the two basic sub-classes of proteases, exopeptidases causing a proteolytic digestion of polypeptides from their N-/C-termini inwards, and endopeptidases causing a proteolytic digestion of polypeptides at specific amino acid sequences within the polypeptide.

Endopeptidases can be particularly useful since they act to provide additional information about the sample polypeptide when the at least one putative amino acid sequence is created or reviewed, and in particular can be used to confirm that a specific sequence or sequences must be present in the sample polypeptide.

For example, the endopeptidase trypsin can be used in the present invention. Other useful endopeptidases are well known and will be readily apparent to the skilled person.

In the method of the invention, the plurality of candidate m/z peak sets can be identified at step (ii) by:
  (a) from the set of m/z peaks obtained in step (i) having x peaks, identifying every possible candidate m/z peak set having between 2 and x members; and
  (b) discarding every candidate m/z peak set having a mass difference between any one of its m/z peaks and its at least one neighbor which is not equal to the mass of an amino acid.

For example, at step (b), it is possible to determine in each candidate m/z peak set the mass difference between each m/z peak and its at least one neighbor, and to then discard every candidate m/z peak set having any mass difference which is not equal to the mass of an amino acid.

Thus a choice can be made between identifying only a certain number of possible candidate m/z peak sets, and determining all possible candidate m/z peak sets. The latter is obviously the more thorough of the two options, and particularly in the situation where nothing is known about the sample polypeptide it is typically the preferred option. If, however, anything is known about the sample polypeptide, such as terminal amino acid sequence, then it is possible to use only those sets of candidate m/z peaks conforming with the known information about the polypeptide.

Such filtering can, of course, be applied at any convenient stage in the process of determining the at least one putative amino acid sequence. And issues such as programming simplicity, flexibility, and/or resource usage may be taken into consideration when determining the point or points at which any filtering is to be done.

The generating of sets of candidate m/z peaks can also be affected by the amino acid masses with which the mass differences are compared. For example, the set of amino acid masses may simply consist the masses of standard amino acids. Alternately, if it is known that a sample polypeptide does not comprise a certain amino acid then the mass of that certain amino acid can be excluded. Similarly, amino acid masses of e.g. chemically and/or post-translationally modified amino acids can also be used. The masses of other amino acids, both naturally occurring and synthetic, can also be used, and can include modified and unusual amino acids such as 2-aminoadipic acid, 2-aminobutyric acid, isodesmosine, 6-n-methyllysine, and norvaline. Others are listed in for example Table 4 of WIPO Standard St.23. Similarly, allowance can be made for isotopically labeled amino acids.

Obviously, if a given amino acid is known not to be in the sample polypeptide then as an alternative to excluding its mass from the set of amino acid masses available for determining candidate m/z peak sets, the candidate m/z peak sets can be generated anyway and any which include the given amino acid can be discarded. This is, however, more computationally complex than excluding its mass from the set of amino acid masses available for determining candidate m/z peak sets and so may not be a preferred option.

The filtering process employed at step (iii) is referred to as the "Reflective Predicate Filter" and is not suggested anywhere in the art. It is particularly useful in that it correlates sets of daughter ions generated by the mass spectrometry—if an at least partial reverse-order mass difference sequence does not exist for a mass difference sequence determined for a candidate set of m/z peaks then the candidate m/z peak set is discarded. This step essentially removes from the sets of candidate m/z peaks (i.e. candidate amino acid sequences) those which include inappropriate daughter ions. For example, a set of m/z peaks each separated by the mass of an amino acid might include a number of b-daughter ions, together with an x-daughter ion. If the set of peaks consisted solely of b-daughter ion peaks then a complementary set of y-daughter ion peaks separated by the same mass differences should exist and therefore the candidate sequence would not be discarded. However, in the case of a set of b-daughter ions and an x-daughter ion, the complementary set of mass peaks would have to consist of a set of y-daughter ions and an a-daughter ion, and the mass differences would not correspond to those of amino acids or would be otherwise incorrect, and thus the candidate sequence having the x-daughter ion would be discarded. In the present context, "at least part" means at least 2, 3, 4, 5, 6, 7, 8, 9, 10, 15, 20 or 25 mass differences of the mass difference sequence of another amino acid. Of the two compared sequences, one must be a contiguous sub-sequence of the other.

At step (iv), Difference Sets can be identified in a number of ways, which can be broadly split up into deductive and inductive processes. The deductive processes use logical rules to determine how the m/z peak sets should be interpreted. A first deductive process for determining Difference Sets comprises the steps of:

(a) comparing each of the remaining candidate m/z peak sets;

(b) correlating the results of comparison step (a) to identify any Difference Sets comprising a first of said candidate m/z peak sets which forms at least part of a second of said candidate m/z peak sets displaced by any one of the group consisting of −17 u, −18 u, −34 u and −48 u; and (c) labeling the members of any −17 u Difference Sets as putatively containing an amino acid selected from the group consisting of: Asparigine, Glutamine, Lysine and Arginine, labeling the members of any −18 u Difference Sets as putatively containing an amino acid selected from the group consisting of: Serine, Threonine, Glutamic acid and Tyrosine, labeling the members of any −34 u Difference Sets as putatively containing a Cysteine amino acid, labeling the members of any −48 u Difference Sets as putatively containing a Methionine amino acid, and labeling the lighter member of each Difference Set as being a neutral loss candidate m/z peak set.

When labeling such Difference Sets, both the first and second candidate m/z peak sets may be labeled regarding their putatively containing the above amino acids.

Alternatively or additionally, Difference Sets can be determined by:

(a) comparing each of the remaining candidate m/z peak sets;

(b) correlating the results of comparison step (a) to identify any Difference Sets comprising a first of said candidate m/z peak sets which forms at least part of a second of said candidate m/z peak sets displaced by any one of the group consisting of +28 u, +17 u and −26 u; and (c) labeling the heavier and lighter of any +28 u Difference Sets respectively as putative b- and a-Difference Sets, labeling the heavier and lighter of any −26 u Difference Sets respectively as putative x- and y-Difference Sets, and labeling the heavier and lighter of any +17 u Difference Sets respectively as putative c- and b-Difference Sets.

The amino acid sequences represented by the candidate m/z peak sets can be determined by a simple look-up of the mass differences between the m/z peak values against a set of amino acid masses. Thus a set of m/z peak values can be readily translated into an amino acid sequence. This can be done starting from the heaviest m/z peak value or from the lightest or in any other order. However, the resultant sequence still needs to be assigned a directionality—the ion species from which the sequences are determined could be a-, b-, or c-ions which will give, going from the heaviest m/z peak value to the lightest, an amino acid sequence in the direction C to N. Alternatively, the ion species from which the sequences are determined could be x-, y-, or z-ions which will give, going from the heaviest m/z peak value to the lightest, an amino acid sequence in the direction N to C. Amino acid sequences are commonly represented in the N to C direction and sequence derived from a-, b- and c-ion species must not be confused with sequence derived from x-, y- and z-ion species.

Thus a step in the process of determining a putative amino acid sequence can be to determine the directionality of the amino acid sequences represented by the candidate m/z peak sets, and this can be done as discussed by Papayannopoulos, IA (supra). By determining the precursor mass for the sample polypeptide and the known candidate m/z peak set values, the heaviest values in each of the sets can be compared with the precursor ion mass to identify any differences which correlate to the mass of an amino acid, or to the mass of an amino acid +18 u. If a candidate m/z peak set is found whose greatest m/z peak value is equal to the sample polypeptide precursor mass minus the mass of an amino acid then the candidate m/z peak set is a y-series whose C-terminal member is the amino acid corresponding to the mass difference. Alternatively, if a candidate m/z peak set is found whose greatest m/z peak value is equal to the sample polypeptide precursor mass minus 18 and minus the mass of an amino acid then the candidate m/z peak set is a b-series whose N-terminal member is the amino acid corresponding to the mass difference plus 18.

The step of determining the directionality can be referred to as being the Classification Predicate. Once an m/z peak set has been identified as being a-, b-, c-, x-, y- or z-series (but particularly a b- or y-series) (and thus its directionality determined), Difference Sets from the series can then be identified, and can be used for scoring below).

Thus the method of the present invention may additionally comprise the step of determining the precursor mass for the sample polypeptide. The precursor mass may also be useful for reasons other than the identification of Difference Sets and so may in any event be determined.

Thus alternatively or additionally, Difference Sets can be determined by:
 (a) with the remaining candidate m/z peak sets, calculating the difference between the heaviest m/z value in each candidate m/z peak set and said precursor mass of said sample polypeptide;
 (b) comparing the differences with the masses of amino acids and with the masses of amino acids +18 u; and
 (c) correlating the results of comparison step (b), a difference equal to the mass of an amino acid indicating a y-series Difference Set having the amino acid at its C-terminus, and a difference equal to the mass of an amino acid +18 u indicating a b-series Difference Set having the amino acid at its N-terminus.

Thus the direction of a candidate m/z peak set can be determined, and thus so can the direction of a putative amino acid sequence derived from the candidate m/z peak set.

In particular the combination of the above three deductive processes to identify Difference Sets can provide valuable information allowing the determination of putative amino acid sequences for the sample polypeptide.

As well as acting as a filter to simplify the candidate m/z peak sets, the identification of Difference Sets can also be used as the basis of a scoring system in order to allow the allocation of a score to each remaining candidate m/z peak set (i.e. to each putative amino acid sequence). Thus when the results of the method of the present invention are determined, they can be provided together with their scores.

For the various series, and particularly for b- and y-series, scores can be calculated by counting the number of Displacement m/z values (i.e. Displacement Masses) for each series, and comparing this with the number of m/z values in the respective series (as appropriate), e.g. b- and y-series, the greater the number of possible Displacement m/z values found for the number of m/z values in the series (e.g. b- or y-series), the greater the likelihood of the sequence being correct, and therefore a score can be allocated as appropriate.

For example, scores can be calculated by counting the number of Displacement m/z values (Displacement Masses) for each Displacement Series obtainable from each main series, and dividing this by the number of m/z values in the main series, giving a value of <=1 for each Displacement Series. Thus for example with a main b-series having 5 masses, and an b-18 series having 3 masses, a score of 3/5 (0.6) is given.

In the case of b-series, a-series Displacement Masses can also be included in the b-series score. Thus for a b-series, Displacement Series members of b-17, b-18, a, a-17 and a-18 can be included, corresponding to Displacement Masses of -17, -18, -28, -45 and -46 respectively.

In the case of y-series, only y-series Displacement Masses are included in the y-series score. Thus for a y-series, Displacement Series members of y-17 and y-18 are included, corresponding to Displacement Masses of −17 and −18.

This is further shown in Table 7.

Thus a score can be allotted to each remaining candidate m/z peak set comprising a main a-, b-, c-, x-, y- or z-series, said score being calculated by:
 (a) determining the number of Displacement m/z values in each displacement series obtainable from said main series;
 (b) correlating the results of step (a) with the number of m/z values in said main series; and
 (c) allotting a score determined from the result of correlation step (b) to said main series.

In particular, this can be done with a main b- or y-series.

For b-series, an additional scoring factor, based on classifying the highest mass in a series as either the highest mass or the second highest mass in a b-series, can be calculated. For y-series, the highest mass is classified against only a y-series second highest mass, as the highest mass in a y-series is the same as that of the protonated precursor ion mass. If the highest mass in a y-series does not meet this criterion then an attempt to classify the lowest mass in the series as a y1 ion is made. If either of the criteria is met for a b- or y-series then the score can be incremented, for example by 1.0, giving a composite score. The composite scoring process is shown diagrammatically in FIG. 6.

As mentioned above, the present invention can be used with the latest $(MS)^n$ mass spectrometers, where $(MS)^n$ is at least 2, for example 3, 4 or 5, a $(MS)^n$ spectrum (or $(MS)^n$ spectra) constituting that obtained at step (i). With regard to $(MS)^n$ data which is generated for a sample polypeptide, the data consists of a mass spectrum for the sample polypeptide and at least one set of precursor ion mass spectra, each one of these being determined for a selected precursor ion. Candidate m/z peak sets can thus be determined for each precursor ion mass spectrum and they can then all be combined to give the plurality (i.e. the group) of candidate m/z peak sets of step (iii). Alternatively, the candidate m/z peak sets for the precursor mass spectra can be added to their respective precursor parent ions to define extended mass spectra, from each of which can then be determined a plurality of candidate m/z peak sets.

Specifically, in the case of using $MS^n$ spectra where n>2 to generate extended mass spectra, each $MS^n$ spectrum being generated from a precursor ion selected from a parent $MS^{n-1}$ spectrum, the precursor ion having an m/z value, any peak in the parent $MS^{n-1}$ spectrum having an m/z value less than that of the precursor ion is removed from the parent $MS^{n-1}$ spectrum, and the $MS^n$ spectrum is added to the parent $MS^{n-1}$ spectrum to generate a hybrid $MS^n.MS^{n-1}$ spectrum. Thus if a parent $MS^2$ spectrum has 3 precursor ions which are each used to generate an $MS^3$ spectrum then each $MS^3$ spectrum can be used to generate a hybrid $MS^3.MS^2$ spectrum. Thus a total of four spectra can be analysed—the $MS^2$ spectrum and the three hybrid $MS^3.MS^2$ spectra.

If a precursor ion is then selected from one of the $MS^3$ spectra and further ionised and used to generate an $MS^4$ spectrum then this can be used to generate a hybrid $MS^3.MS^4$ spectrum as above (i.e. in this case n=4, and any peak in the parent $MS^{n-1}$ spectrum having an m/z value less than that of the precursor ion is removed from the parent $MS^{n-1}$ spectrum, and the $MS^n$ spectrum is added to the parent $MS^{n-1}$ spectrum to generate a hybrid $MS^n.MS^{n-1}$ spectrum). This hybrid $MS^4.MS^3$ spectrum is then added to the other spectra who share a common lowest $MS^n$ value (in this case n=3), and they in turn are used to generate hybrid spectra with the at least one spectrum having an $MS^n$ value one less than their common lowest $MS^n$ value (i.e. in this case, with the single $MS^2$ spectrum), giving a total of five spectra to be analysed—the $MS^2$ spectrum, the three hybrid $MS^3.MS^2$ spectra, and the single hybrid $MS^4.MS^3.MS^2$ spectrum.

Obviously, this methodology can be extended to any value of n where n>2, for example where n=5, 6, 7, 8, 9 or 10. No fundamental limitations are placed upon the system other than the availability of ion species to act as precursor ions. In practical terms, the methodology does have the potential to provide for a substantial increase in the number of spectra to be analyzed and therefore the volume of data to be analyzed. However, the various filter predicates of the present invention, particularly the Mass Difference Predicate (step (ii)) and the Reflective Predicate (step (iii)) readily reduce the volume of data and the number of putative amino acid sequences which are generated.

Thus the use of $MS^n$ spectra where n>2 can result in a tree-like data structure (i.e. in which normal recursive navigation can be effected), with a spectrum for analysis being generated at the tree trunk (n=2) and hybrid spectra being generated at each branch. This recursive iteration of the possible spectra and the generation of a "tree" type structure of spectra is shown at FIGS. 8-13.

The generation of such spectra and hybrid spectra can be expressed as follows:

The above method for determining putative amino acid sequences for a sample polypeptide can be considered to comprise a deductive process. However, the present invention also extends to the use in inductive processes to determine putative amino acid sequences. In particular, supervised machine learning algorithms can be used in order to determine putative sequences from MS and $(MS)^n$ data.

In addition or alternatively, inductive methods may be employed to identify Difference Sets, particularly ion series. For example, Difference Sets (e.g. ion series) may be determined by:

(a) passing the remaining candidate m/z peak sets as an input to a computer executing program code for a supervised learning algorithm, said supervised learning algorithm being trained to identify Difference Sets; and (b) outputting identified Difference Sets in said remaining m/z peak sets from said computer.

Supervised learning algorithms useful in the present invention include k-NN (T. M. MITCHELL, "Machine Learning", McGraw-Hill International Editions, 1997), C4.5 (J. R. QUINLAN, "C4.5: Programs for Machine Learning", MorganKaufmann, 1993), CN2 (P. CLARK, T. NIBLETT, "The CN2 induction algorithm", Machine Learning, 3(4):261-283, 1989; P. CLARK, R BOSWELL, "Rule induction with CN2: some recent improvements", in Proceedings of ECML'91, pp. 151-163, 1991; R. RAKOTOMALALA, D. ZIGHED, F. FESCHET, "Empirical evaluation of rule characterization in rule induction process", in Proceedings of the Fourteenth European Meeting on Cybernetics and Systems Research, pp. 779-804, 1998), RBF (Radial Base Function neural network), and OCI (Murthy SK et al., "A System for Induction of Oblique Decision Trees", Journal of Artificial Intelligence Research 2(1994) 1-32).

To briefly review the above algorithms, the k-NN algorithm compares an unknown data point (from within a new data set) with k nearest neighbors from previously classified data points. With this method, the k nearest neighbors to the unknown point are most likely to be from the point's proper population. With this algorithm it may be necessary to reduce the weight attached to some variables by suitable scaling, such that at one extreme variables may be removed completely if they don't contribute usefully to the discrimination. This can be determined and addressed experimentally.

The C4.5 algorithm generates decision trees to effectively generate tests to partition data. The algorithm uses an entropy based measure in order to determine the quality of the tests available. However, this alone would favor tests, which reduce the level of uncertainty of the class so C4.5 also uses a modified measure to ensure that it is not biased towards tests with many outcomes. The advantage that this algorithm has over others is that it supports estimated error-basedpruning so ensuring that the performance is not reduced due to overfitting.

The CN2 algorithm has a key advantage over similar methods in its class, namely that it has an ability to cope with 'other complications' in the data. During its search for complexes CN2 does not automatically remove from consideration candidates which are included in more than one negative example. It reassigns a set of complexes in its search which is evaluated statistically as covering a large number of examples of a given class and few of other classes. The manner in which CN2 conduct a search is generic-to-specific. Each trial specialization step takes the form of either adding a new conjunctive term or removing a disjunctive term. Once CN2 has found a good complex, the algorithm removes those examples it covers from the training set and adds if <complex> then predict <class> to the end of the rule list. The process terminates for each given class when no more acceptable complexes can be added to the list.

The RBF algorithm is based on neural network technology where a network of nodes is generated that emulate the operation of the human synaptic nerve junction—these are known as nodes. The RBF network consists of a layer of nodes, which perform linear or non-linear functions of the attributes, followed, by a layer of weighted connections to the nodes whose outputs have the same form as the target vectors. It has a structure similar to the Multilayer perception (MELP) except that each node of the hidden layer computes n arbitrary functions of the inputs, and the transfer function of each output node is the trivial identity function. The hidden layer has parameters appropriate for whatever functions are being used such as Gaussian widths and positions.

The main advantages that the RBF algorithm has over other neural net algorithms are that it includes a linear training rule once the locations in attribute space of the non-linear functions have been determined, an underlying model including localized functions in the attribute space, rather than long-range functions occurring in other models. The linear learning rule avoids problems associated with local minima, especially since this enables the enhanced ability to make statements about the probabilistic interpretation of the outputs.

OC1 is a machine learning, decision tree algorithm, which, unlike C4.5, makes its decisions on various boundaries based upon single attributes (termed oblique decisions).

The OC1 uses linear combinations of attributes in decision making and requires all attributes to be numeric.

Each supervised learning algorithm, when running as part of a computer program, needs to be provided with a training data set in order that it can learn to interpret new sets of data with an acceptable probability that it will return the correct results—this process (of learning from a training data set and then using it to make predictions and/or classifications of another data set) is referred to as "generalisation". The process of generalization allows the partitioning of data into a series of pre-defined classes (such as b- or y-Difference Sets)

Since the supervised learning algorithm is to determine the identity of Difference Sets, the training data needs to comprise Difference Sets, e.g. a-, b-, and y-ion series. Training data can also comprise negative examples of m/z peak sets, as well as data for other Difference Sets such as x- and z-ion sets. Similarly, training data can be provided for e.g. w-Difference Sets. Training data can also be used representing neutral loss sets.

Also provided according to the present invention is a method for using a computer to determine at least one putative amino acid sequence for a sample polypeptide, said sample polypeptide being partially degraded, said method comprising the steps of:

(i) obtaining a soft ionisation mass spectrum of said sample polypeptide giving a set of m/z peaks of ion species obtained from said partially degraded sample polypeptide;

and with said computer:

(ii) with said set of m/z peaks obtained in step (i), determining a plurality of candidate m/z peak sets, each m/z peak in each candidate m/z peak set differing from its at least one neighbor by the mass of an amino acid;

(iii) with each candidate m/z peak set determined at step (ii), determining a sequence of mass differences between each m/z peak and its at least one neighbor and discarding any candidate m/z peak sets whose mass difference sequence in reverse order does not form at least part of the mass difference sequence of another of said candidate m/z peak sets;

(iv) identifying any Difference Sets in the remaining m/z peak sets;

(v) with the remaining candidate m/z peak sets, identifying and discarding any candidate m/z peak set which is a contiguous subsequence of another candidate m/z peak set; and (vi) determining a putative amino acid sequence for each remaining candidate m/z peak set, each amino acid sequence being that of the amino acids which correspond to the mass differences between each m/z peak and its at least one neighbor, each putative amino acid sequence comprising an at least partial putative amino acid sequence of said sample polypeptide.

The mass spectrum can be simply supplied as a data set from a mass spectrometer located locally or remotely, and can for example be a mass spectrum stored on a computer database or another storage medium.

The computer may return its results in any desired form, e.g. as an at least one putative sequence, optionally with any value score or scores as discussed above, or e.g. such as statistical data, regarding the at least one putative amino acid sequence.

Also provided is a system for determining at least one putative amino acid sequence for a sample polypeptide, said sample polypeptide being partially degraded, said system comprising:

(a) a memory for storing machine instructions for:

(i) with a set of m/z peaks obtained from a soft ionization mass spectrum of said sample polypeptide giving said set of m/z peaks of ion species obtained from said partially degraded sample polypeptide, determining a plurality of candidate m/z peak sets, each m/z peak in each candidate m/z peak set differing from its at least one neighbour by the mass of an amino acid;

(ii) with each candidate m/z peak set determined at step (i), determining a sequence of mass differences between each m/z peak and its at least one neighbour and discarding any candidate m/z peak sets whose mass difference sequence in reverse order does not form at least part of the mass difference sequence of another of said candidate m/z peak sets;

(iii) identifying any Difference Sets in the remaining m/z peak sets;

(iv) with the remaining candidate m/z peak sets, identifying and discarding any candidate m/z peak set which is a contiguous subsequence of another candidate m/z peak set; and (v) determining a putative amino acid sequence for each remaining candidate m/z peak set, each amino acid sequence being that of the amino acids which correspond to the mass differences between each m/z peak and its at least one neighbor, each putative amino acid sequence comprising an at least partial putative amino acid sequence of said sample polypeptide; and (b) a processor that is coupled to said memory, said processor executing said machine instructions, causing said processor to determine at least one putative amino acid sequence for said sample polypeptide.

Also provided is a computer program for determining at least one putative amino acid sequence for a sample polypeptide, said sample polypeptide being partially degraded and a soft ionisation mass spectrum of said sample polypeptide having been obtained giving a set of m/z peaks of ion species obtained from said partially degraded sample polypeptide, said computer program comprising:

(i) program code for determining a plurality of candidate m/z peak sets, from said set of m/z peaks, each m/z peak in each candidate m/z peak set differing from its at least one neighbor by the mass of an amino acid;

(ii) program code for determining from each candidate m/z peak set determined at step (i) a sequence of mass differences between each m/z peak and its at least one neighbor, and for discarding any candidate m/z peak sets whose mass difference sequence in reverse order does not form at least part of the mass difference sequence of another of said candidate m/z peak sets;

(iii) program code for identifying any Difference Sets in the remaining m/z peak sets;

(iv) program code for identifying and discarding from the remaining candidate m/z peak sets any candidate m/z peak set which is a contiguous subsequence of another candidate m/z peak set; and (v) program code for determining a putative amino acid sequence for each remaining candidate m/z peak set, each amino acid sequence being that of the amino acids which correspond to the mass differences between each m/z peak and its at least one neighbour, each putative amino acid sequence comprising an at least partial putative amino acid sequence of said sample polypeptide.

Also provided is a computer program product for determining at least one putative amino acid sequence for a sample polypeptide, comprising a computer usable medium having computer readable program code means according to the present invention embodied in said medium.

The computer program code for identifying Difference Sets in the remaining m/z peak sets can be written in any appropriate language, but the present inventors have found that Logic Programming languages such as Prolog are particularly useful and effective in the present invention.

The invention will be further apparent from the following description, with reference to the several figures of the accompanying drawings, which show, by way of example only, one form of determining a putative amino acid sequence from a set of m/z peaks.

OF THE FIGURES

Figure 6:
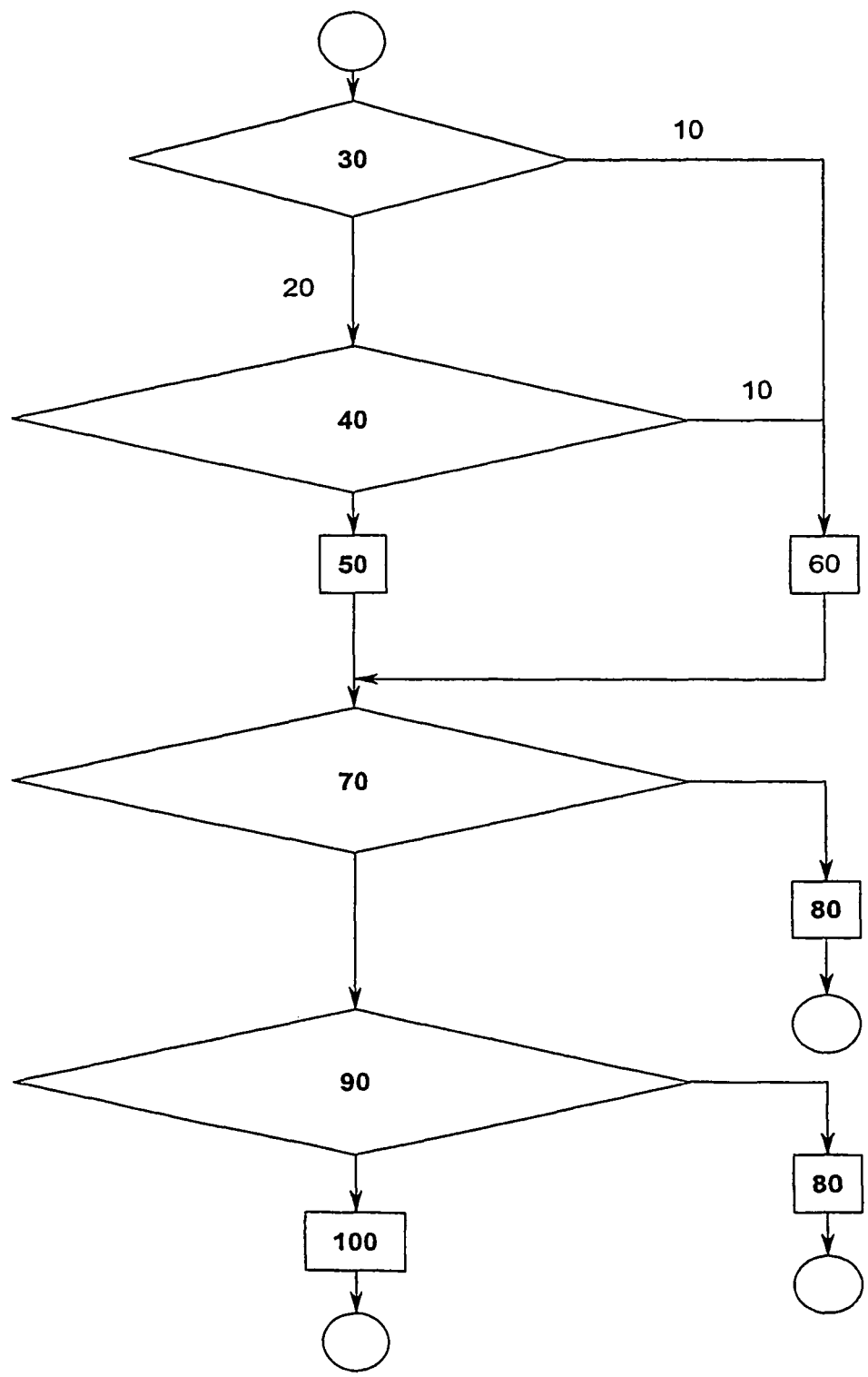
Figure 8:
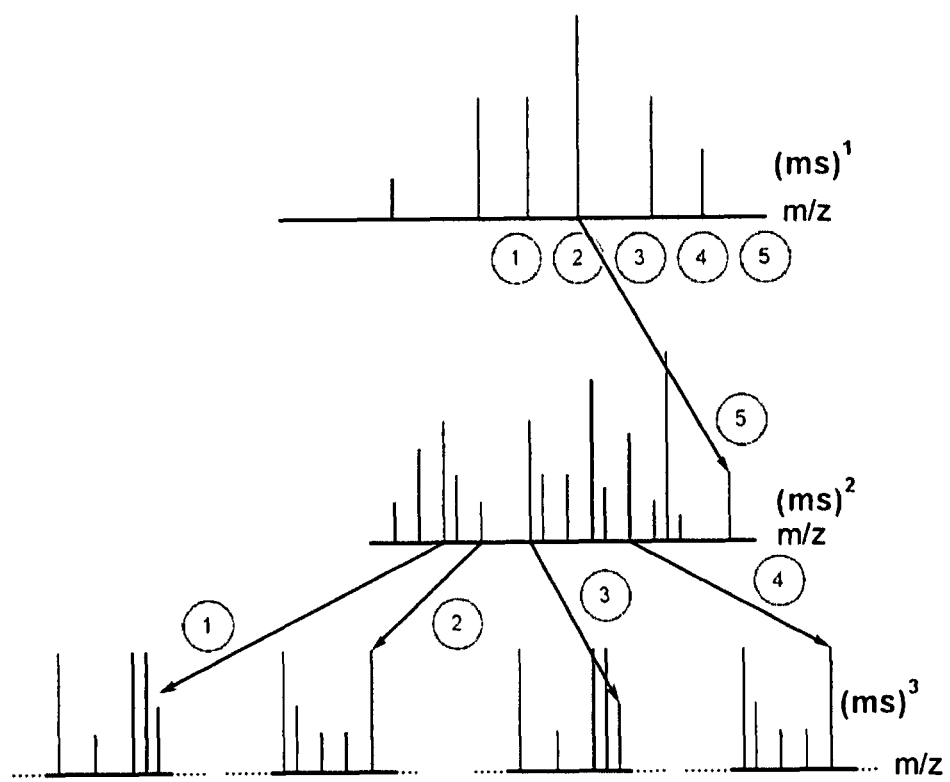
Figure 9:
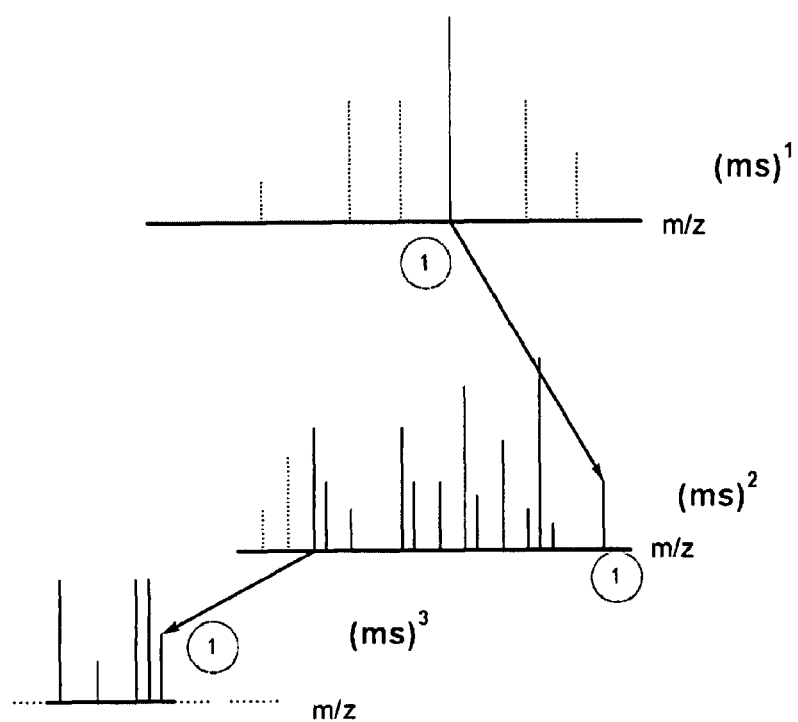
Figure 10:
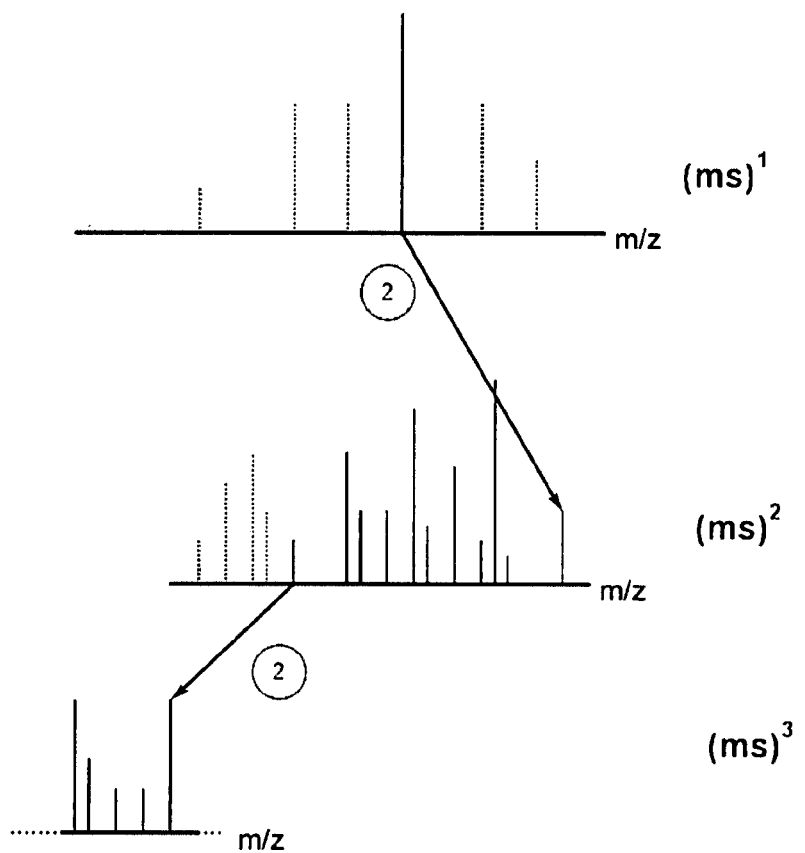
Figure 11:
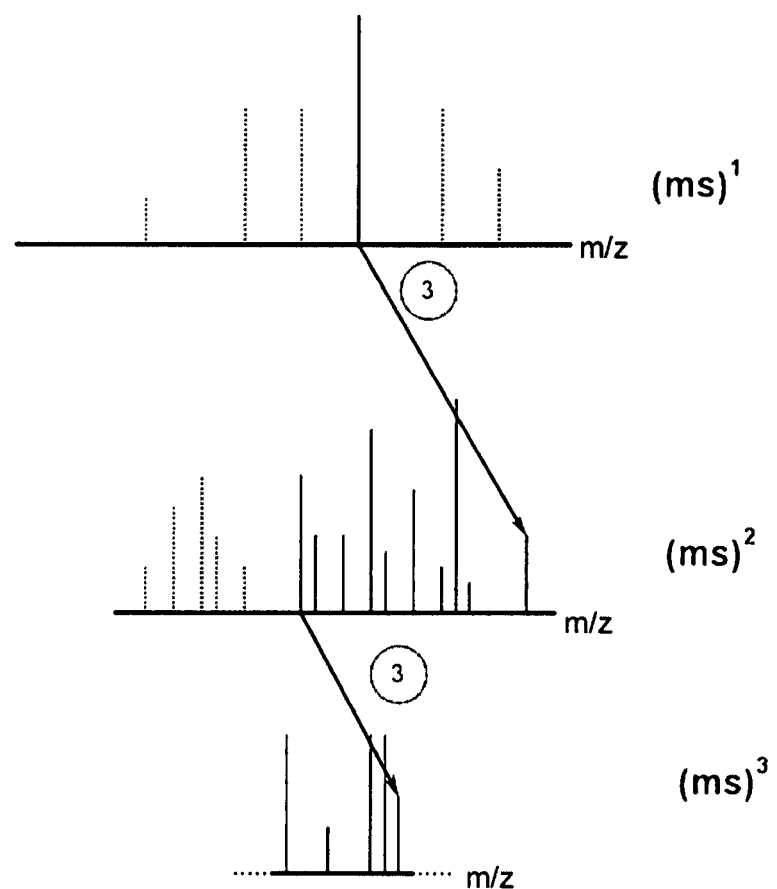
Figure 12:
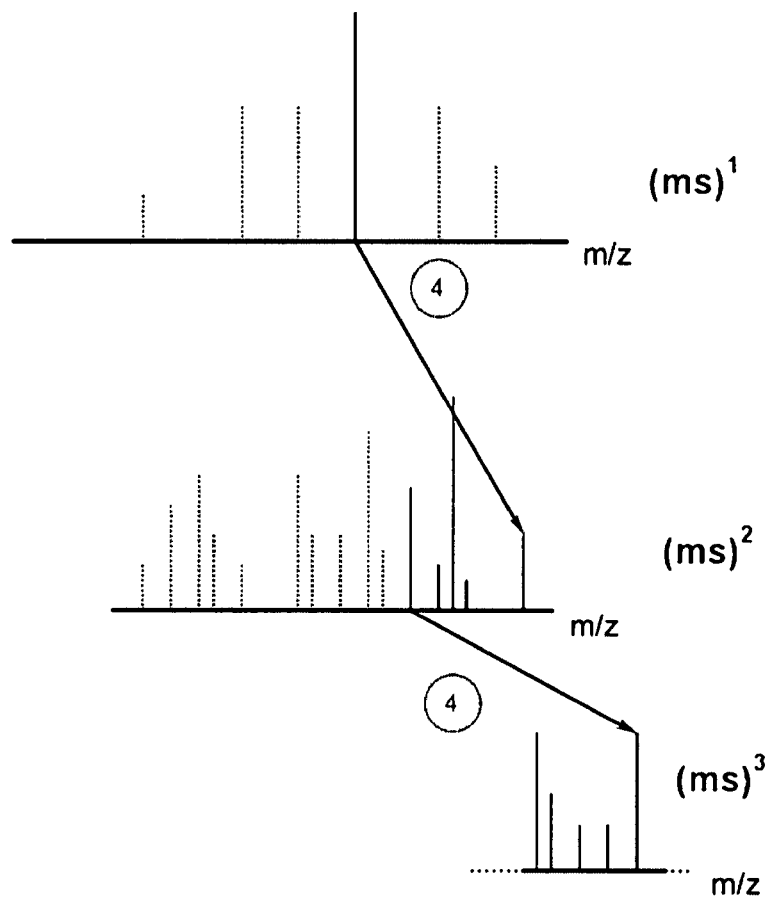
Figure 13:
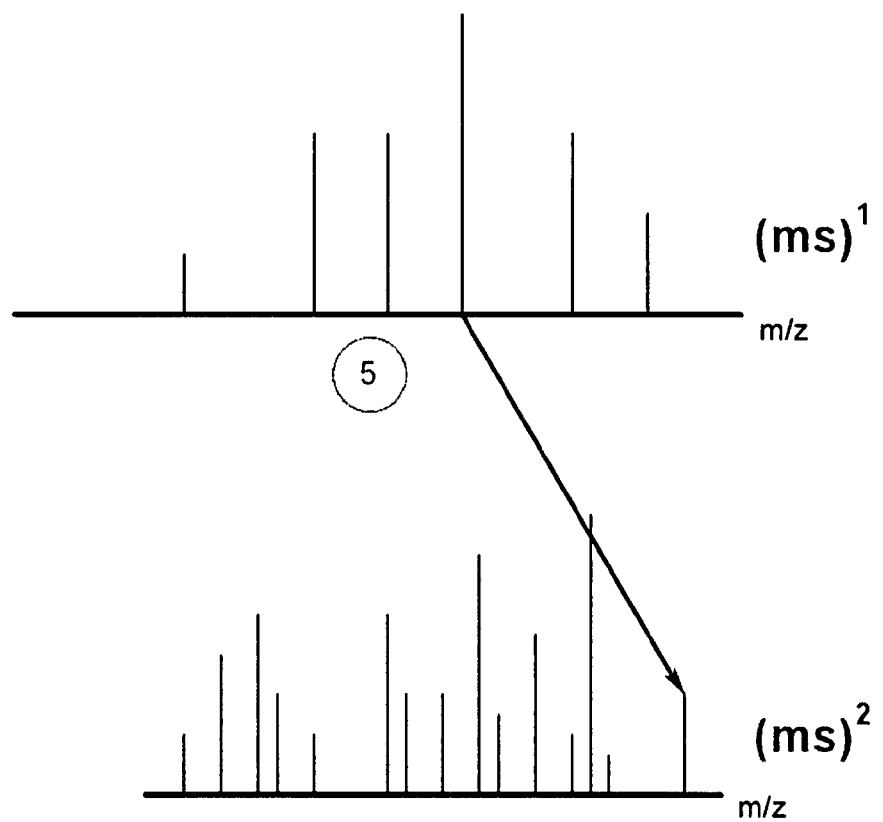

FIG. 3 shows a table of amino acid properties. Columns are as follows: A—3 letter amino acid code; B—empirical formula; C—monoisotopic mass (H=1.00782504, C=12.0000000, N=14.0030740, O=15.9949146, S=31.9720710); D—average mass (H=1.0079, C=12.011, N=14.007, O=15.999, S=32.066); E—side chain [nominal]; F—structure; G—Neutral loss (T. Madden, et al., Org. Mass Spectrom., 26, 443 (1991)) [nominal]; H—Immonium ion(s) (K. Ambihapathy, et al., J. Mass Spectrom., 32, 209 (1997), immonium ions being measured by FABMS (Pos.)) [nominal]; I—immonium ion relative intensity (W=weak, S=strong, V=very strong); J—type (A=apolar, U=uncharged polar, C=charged polar); K—Bull & Breese values (H. B. Bull, K. Breese, Archives Biochem. Biophys., 161, 665-670 (1974)); L—isoelectric point; M—occurrence (see for example prowl.rockefeller.edu/aainfo/contents.htm;

FIG. 4 shows (A) the basic structure of an amino acid, (B) an example representation of the structure of glycine, (C) the basic structure of a $y_j$ ion, and (D) the basic structure of a $b_j$ ion;

FIG. 5 shows (A) the basic structure of an $x_j$ ion, (B) the basic structure of an $a_j$ ion, (C) the z-series ionisation mechanism, $r_j^b$ and $r_j^a$ being alternatives to one another, and (D) the c-series ionisation mechanism;

FIG. 6 shows a composite scoring system for adjusting the scores allocated to top values in a b-series and y-series and for a $y_1$ ion;

FIG. 7 shows a logic-based Karnaugh map used in determining b- and y-series classification. In Series 1 and Series 2, letters with a —(bar) above them indicate not classified as the series;

FIG. 8 shows a complex $(MS)^n$ tree structure showing 4 possible putative series paths labelled 1-4;

FIG. 9 shows Path 1 putative series masses;

FIG. 10 shows Path 2 putative series masses;

FIG. 11 shows Path 3 putative series masses;

FIG. 12 shows Path 4 putative series masses;

FIG. 13 shows Path 5 putative series masses using only $(ms)^2$ data; and

Figure 14:
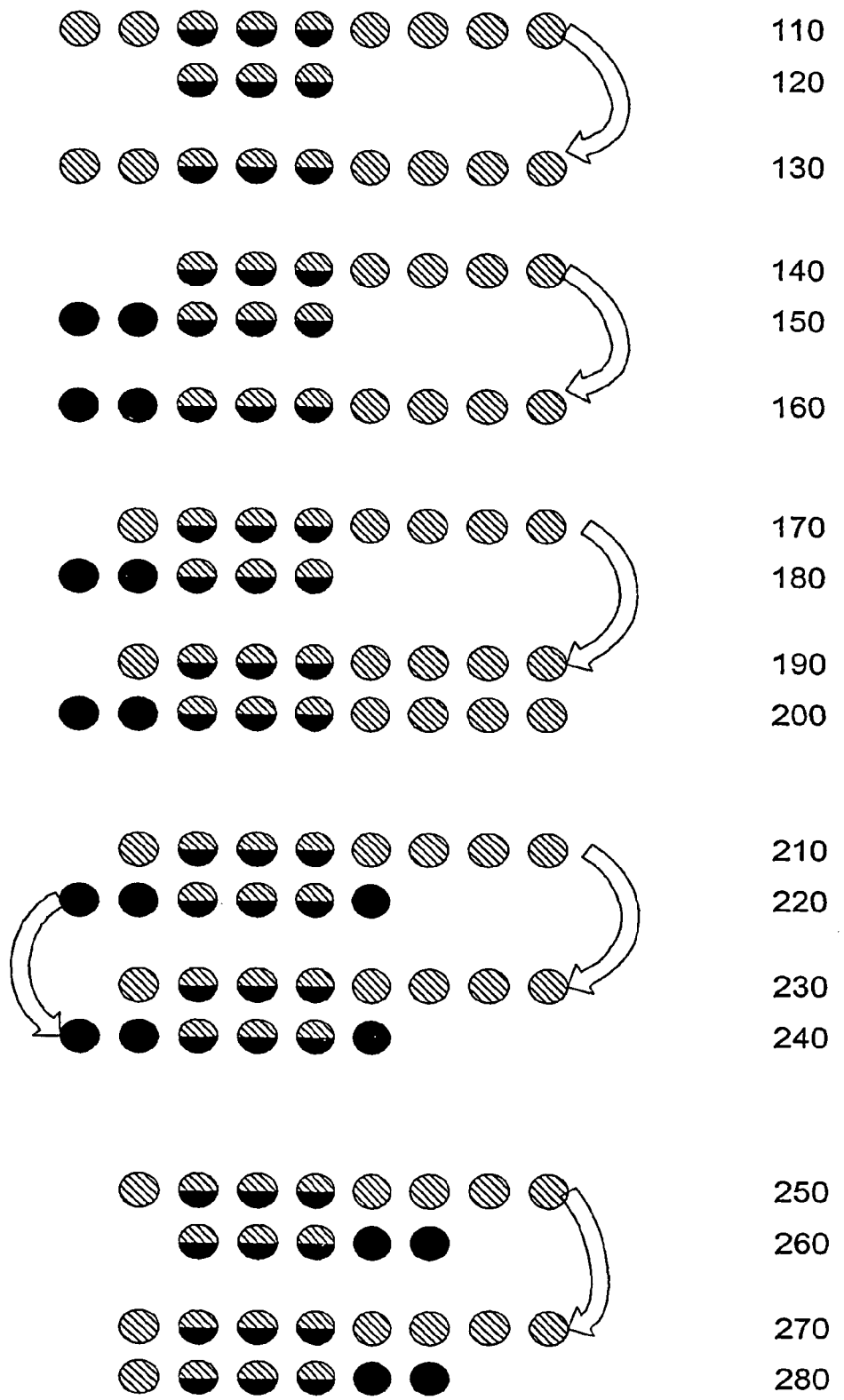

FIG. 14 shows splicing of N- and C-terminal series

EXAMPLES

The following example demonstrates how a putative amino acid sequence is determined from a set of m/z peaks. All amino acids (with the exception of proline) terminate in the group $NH_2CHRCOOH$ wherein R denoted a side chain. This basic structure can be represented diagrammatically as shown in FIG. 4A, and an example representation of the structure of glycine is given at FIG. 4B.

Figure 2:
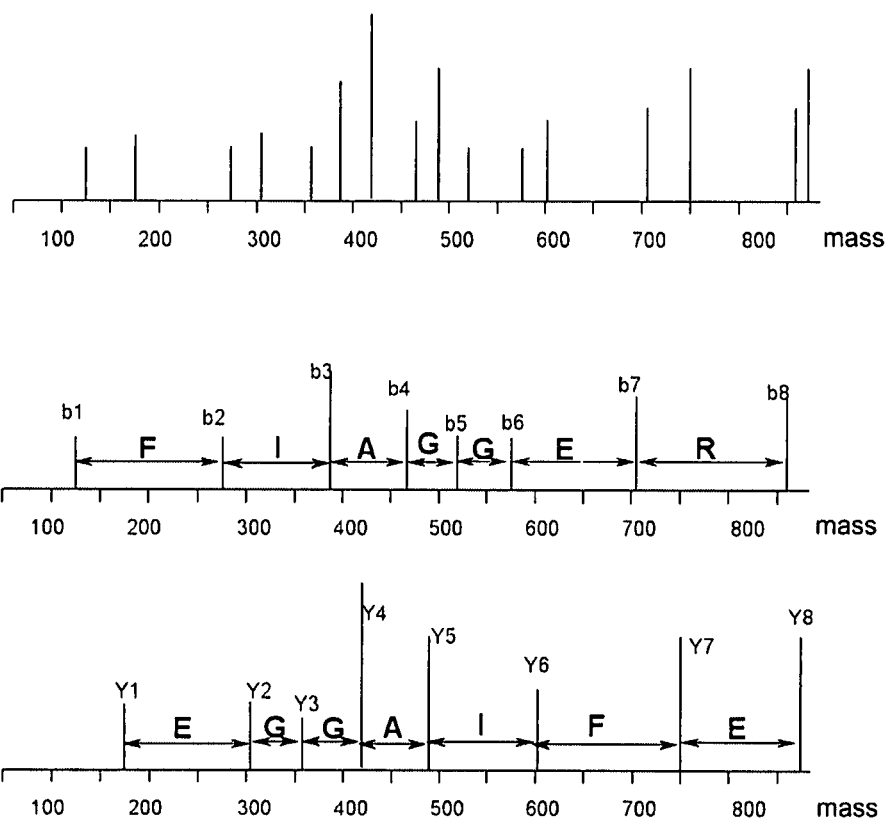
FIG. 2 shows an example set of m/z peaks from which a putative amino acid sequence is determined. The sequence of SEQ ID NO: 1 is deduced by classifying a compound spectrum (top) into ion species spectra (middle and bottom)

Starting with the set of m/z peaks shown in the mass spectrum of FIG. 2, the following equations are used. Note that they are different to those defined in Scheme 4 of the Papayannopoulos, IA (supra) paper. The basic structure of a $y_j$ ion is given at FIG. 4C, and that for a $b_j$ ion at FIG. 4D.

$$y_j = [C\ \text{term}] + \sum_{i=(n-j+1)}^{n} aa_i + [H] + [H^+]$$

$$b_j = [N\ \text{term}] + \sum_{i=1}^{j} aa_i + [H^+]$$

For unmodified amino acids, where [C-term]=[OH] and [N-term]=[H], these can be re-written to represent a- and x-daughter ions (FIG. 5A is an $x_j$ ion and FIG. 5B is an $a_j$ ion). The equations to represent the masses of these ions are:

$$a_j = [N\ \text{term}] + \sum_{i=1}^{j} aa_i - [CO]$$

$$x_j = [C\ \text{term}] + \sum_{i=(n-j+1)}^{n} aa_i + [CO]$$

FIG. 5C shows the z-series ionisation mechanism. $^aR$ and $^bR$ represent substituents at the beta carbon atom of the amino acid, which lose a hydrogen, which in turn becomes the protonating $H^+$. FIG. 5D shows the c-series ionisation mechanism. Thus:

$$c_j = [N\ \text{term}] + \sum_{i=1}^{j} aa_i + [NH_2] + [H^+]$$

i.e. $c_j = [N\ \text{term}] + \sum_{i=1}^{j} aa_i + [NH_3^+]$ $$z_j = [C\ \text{term}] + \sum_{i=(n-j+1)}^{n} aa_i - [NH] + [H^+] - [H]$$

i.e. $z_j = [C\ \text{term}] + \sum_{i=(n-j+1)}^{n} aa_i - [NH]$ in the above equations, $1 \leq j \leq n-1$ "$aa_i$" denotes the mass of the "i"th amino acid. [N-term], [C-term], [CO], [NH], [NH$_2$], [NH$_3^+$], [H] and [H$^+$] denote the masses of group enclosed therein, i.e. the mass of the group attached to the N-terminus of an amino acid (usually H=1), the group attached to the C-terminus of an amino acid (usually OH=17), CO, NH and NH$_2$.

The above expressions are for the calculation of the mass of singly protonated a-, b-, c-, x-, y- and z-peptide fragment ions. Subscript j indicates the jth fragment ion of a peptide comprising n amino acids. The numbering of N-terminal fragment ions begins at the N-terminus, and the numbering of C-terminal fragment ions begins at the C-terminus. Therefore the jth N-terminal fragment ion of a peptide has a mass comprised of the sum of the masses of the first j amino acids. In contrast, the jth C-terminal fragment ion of a peptide has a mass comprised of the sum of the masses of the last j amino acids.

From the above equations it can be deduced that:

$$a_j - a_{j-1} = aa_j$$

$$x_j - x_{j-1} = aa_{n-j+1}$$

$$b_j - b_{j-1} = aa_j$$

$$y_j - y_{j-1} = aa_{n-j+1}$$

$$c_j - c_{j-1} = aa_j$$

$$z_j - z_{j-1} = aa_{n-j+1}$$

Thus the differences in the series of m/z peaks generated from a mass spectrum of a sample polypeptide will follow the pattern of amino acid masses in the sequence of the sample polypeptide. These equations are referred to herein as the "Difference Equations".

In addition, the following Series Difference Equations can be derived:

$$b_j - a_j = [CO] = 28$$

$$b_j - c_j = [NH_3] = 17$$

$$y_j - x_j = [H_2] - [CO] = -26$$

$$y_j - z_{j-[H2]} + [NH] = 17$$

Precursor Ion Relationships

Relationships with the precursor ion mass can also be determined as follows:

Adding the $b_j$ and $y_j$ equations and assuming that [N term]=[H] and that [C term]=[OH] the following results:

$$b_j + y_{n-j} = \sum_{i=1}^{n} aa_i + [OH] + [H] + [H^+] + [H]$$

The mass of the protonated precursor ion can be calculated as follows:

$$[\text{precursor ion}] = \sum_{i=1}^{n} aa_i + [OH] + [H] + [H^+]$$

in which the [H$^+$] arises as the precursor ion is protonated.

Thus, $b_j + y_{n-j} = [\text{precurser ion}] + [H]$

Electrospray Doubly Charged Ion Relationships

Relationships with electrospray doubly charged ions can be determined as follows, electrospray samples usually containing an intense doubly charged peak.

$$[\text{precursor ion}] = \left( \sum_{i=1}^{n} aa_i + [OH] + [H] + [H^+] + [H^+] \right) / 2$$

Thus, $b_j + y_{n-j} = 2 * [\text{precursor ion}]$

Largest Series Ion and Precursor Relationships

Given that $1 \leq j \leq n-1$, the following can be derived:

$$[\text{precursor ion}] - [b_{n-1}] = \sum_{i=1}^{n} aa_i + [OH] + [H] + [H^+] - \left( \sum_{i=1}^{n-1} aa_i + [H] \right)$$

i.e. $[\text{precursor ion}] - [b_{n-1}] = aa_n + [OH] + [H^+]$ and $$[\text{precursor ion}] - [y_{n-1}] = aa_2 + [OH] + [H] + [H^+] - [OH] - [H_2]$$

i.e. $[\text{precursor ion}] - [y_{n-1}] = aa_2$

The top spectrum in FIG. 2 shows 16 mass peaks which can in turn be used to determine a very large number of sets of masses, each containing between 2 and 16 of the mass peaks shown and which might correlate with the sequence of the sample polypeptide. The total number of sets m/z peaks, denoted by M, is represented as:

$$\sum_{i=1}^{16} {}^{16}{}_iP$$

The deductive method works by determining a subset $m_{DN}$ (DN is short for De-Novo) of M by using predicate calculus concepts. Predicate calculus is a mathematical method derived from boolean algebra and is well known in the art.

The following statement is true: $\forall m_{DN} \in M$ i.e. each $m_{DN}$ set is a subset of M. ($\forall$ meaning "for all", and $\epsilon$ denoting a subset).

Thus the $m_{DN}$ sets are deduced using the predicate that each member in the set must be one amino acid different in mass from its neighbouring at least one element (the "Mass Difference Predicate"). This satisfies the Difference Equations (above). As discussed above, the set of amino acid masses which are made available for the predicate can be those of the standard amino acids or can, if desired, include masses for unusual or modified amino acids, or can exclude certain amino acids—the decision as to which masses are to be included and which are to be excluded can be made on the basis of available information about the sample polypeptide, or for example the culture conditions of a micro-organism producing the sample polypeptide which mean that e.g. isotopically labelled versions of amino acids may be comprised in the sample polypeptide.

A mass spectrum of a sample polypeptide having the sequence of SEQ ID NO: 1 (REGGAIFE) results in the set of m/z peaks having the values 147, 185, 197, 213, 215, 225, 243, 262, 296, 324, 333, 342, 409. 437, 455, 462, 489, 506, 524, 538, 542, 577, 659, 664, 777, 846, 864, 959, 977 and 1076. Candidate m/z peak sets are then derived as shown in Table 1.

To do this, a computer program searches for solutions to the Mass Difference Predicate and is presented with the set of m/z peak values detailed in Table 1 by first selecting a root (or "starting point") mass. The highest mass is used—in the case of Table 1 this is mass 1076. It then looks for all masses that are exactly one amino acid mass lower in mass than the root mass. Each of these masses in turn is used to find further masses that are again separated by amino acid mass values, and this is repeated until there are no more possible solutions.

The process is then repeated with a new root mass—one lower in the series than before. In the case shown in Table 1, this is mass 977. Any new series found are added to the original series found from root mass 1076. The process is repeated right down to the penultimate mass 185.

The results of the process consist the group of candidate m/z peak sets. The computational complexity of the task is very substantial since a vast number of possible solutions to the Mass Difference Predicate must be evaluated, making the task impossible (at least within any kind of a reasonable time frame) for a human, even for a simple set of m/z peaks as shown in Table 1—the present invention is capable of determining candidate m/z peak sets and putative amino acid sequences from much more complex sets of m/z values, and it should be noted that with each additional Z/z value added to the set to be considered, the number of possible sets of m/z values increases in a substantial non-linear manner.

As can be seen from Table 1, a total of 19 basic candidate m/z peak sets are determined. In addition to these (and not shown for the sake of simplicity), contiguous subsequences of each of those shown are also derived and are candidate m/z peak sets which are evaluated using the method of the present invention. An example of a contiguous subsequence is the series y10, y9, y8-18 shown in column 1—the two subsets y10, y9 and y9, y8-18 are also generated and are analysed according to the method of the present invention. Similarly, the set of peaks at m/z values 409, 296 and 197 is also generated and is a subset of the set listed at column 11, but is not shown for the sake of convenience.

The "Series" column of Table 1 shows information about the m/z peaks which has been derived as a result of working the method of the present invention—the only data initially available is the m/z peak data from which the candidate m/z peak sets are determined and which are subsequently analysed and filtered to derive the "Series" information.

Table 1 shows a number of series (i.e. candidate m/z peak sets) including the following 5: [y10,y9,y8,y7,y6,y5,y4,y3,y2,y1] (i.e the m/z peak set 1076, 977, 864, 777, 664, 577, 462, 333, 262, and 147), [y9-18,y8-18] (i.e the m/z peak set 959, and 846), [b5,b4,b3,b2] (i.e the m/z peak set 542, 455, 342, and 243), [b5-18,b4-18,b3-18,b2-18] (i.e the m/z peak set 524, 437, 324, and 225), and [a4-18,a3-18,a2-18] (i.e the m/z peak set 409.296, and 197).

The first letter denotes the ion series type (which, as mentioned above, is subsequently derived but is included here for the sake of convenience—the initial data consists only of m/z peak values) and the second number denotes a mass displacement from the species. For example the b-18 set denotes a b-series, all with a water molecule (mass 18 Daltons) displacement. Certain amino acids will have displaced peaks. Common Displacement Masses are 18 Da ($H_2O$), 28 Da (CO) and 17 Da ($NH_3$).

In order to deduce all possible members of the set $m_{DN}$ a computer program may be employed as follows—the code detailed below is formatted in the Prolog language and searches for all solutions satisfying a set of logical conditions, or predicates, in this case the Mass Difference Predicate. The program language itself uses backtracking methods to find the set of solutions automatically. Thus the identification of the members of the set $m_{DN}$ which fulfill the requirements of the Mass Difference Predicate can be accomplished with the following Prolog code:

RESULT=an empty computation variable that receives the final result amino_diff_set a Prolog goal X=general unknown variable NEXTROOTSEQUENCE=a newly found series NEWSEQUENCE=the new current list of solutions The findall goal (predicate) is used to deduce all possible sequences starting from the root mass (HROOTMASS). The findall goal uses the amino_diff_set goal (predicate) which is able to generate all the sequences starting from a given root mass. All the series found are then added to the existing series using the concat goal. Finally the goal recursively calls itself using the TAILMASSES which are the remaining set of mass peaks after the current highest mass (HROOTMASS) has been removed. The next call to the amino_generator goal will start with a new HROOTMASS, which is one mass down the set of masses from the last time.

Although the above code is formatted for Prolog, a wide range of other languages such as C, C++, C# and PASCAL can also be used to embody the same process (e.g. emulate the same program).

Figure 1:
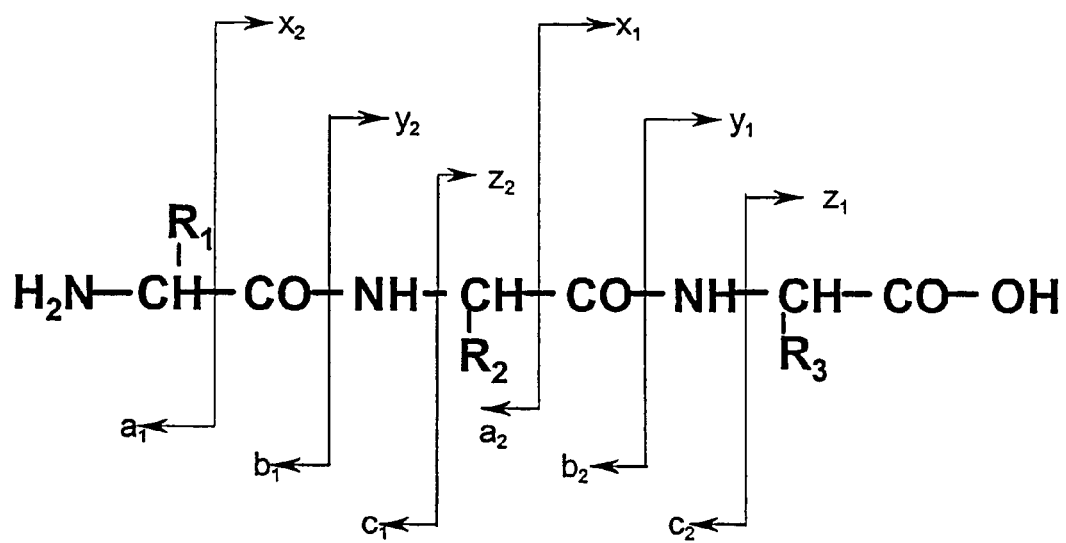
FIG. 1 shows cleavage of an amino acid sequence and the generation of daughter ion species.

Although FIG. 1 demonstrates intact chains of amino acids, it is often the case that one of the ion species is missing and that only part chains exist. The present invention can determine part sequences, providing that they satisfy the Mass Difference Predicate. The ability of the invention to discover part chains comes from the fact that all masses in the original m/z peak set are used as possible starting points or root masses.

Thus the at least one putative amino acid sequence determined by the present invention can comprise at least two putative partial sequences for said sample polypeptide.

Table 1 shows the Mass Difference Predicate solutions for the set of m/z values shown. Four out of five of the correct series have been found, namely the m/z peak sets shown in columns 2, 6, 9 and 15. The set in column 11 is the a-18 series with a further peak at mass 538 added, the peak at 538 not corresponding to SEQ ID NO: 1.

However there are also 14 additional incorrect (or "false") series in the list. Further steps are applied to eliminate false series, and these steps can be regarded as being filtering steps. The filtering steps are also used to classify ion series, deriving the information given in the "Series" column of Table 1.

Reflective Predicate

There are two filtering mechanisms. The first filtering mechanism uses a Reflective Predicate, which is applied to pairs of $m_{DN}$. The sequences of amino acids go in reverse order between a-, b- and c-ions and the x-, y- and z-ions. This property is demonstrated mathematically in the Difference Equations—the C-terminal ions (x-, y- and z-) have the $aa_{n-j+1}$ term, whereas the N-terminal ions have the $aa_j$ term. The reversal or reflected nature of the separation of masses within two $m_{DN}$ sets is demonstrated visually in FIG. 2, the y mass ions set are separated by the sequence EGGAIFE (SEQ ID NO: 2) and the b mass ions set by the sequence FIAGGER (SEQ ID NO: 3), which is the partial reverse of the y set.

Tables 2 and 3 show y- and b-series for a simple peptide LYLKGER (SEQ ID NO: 4).

```
amino_generator([HROOTMASS|TAILMASSES],ACCUMSEQUENCE,RESULT):-
    findall(X,amino_diff_set(HROOTMASS,[HROOTMASS|TAILMASSES],[],X),
NEXTROOTSEQUENCE),
        concat(NEXTROOTSEQUENCE,ACCUMSEQUENCE,NEWSEQUENCE),
        amino_generator(TAILMASSES,NEWSEQUENCE,RESULT).
``` wherein:

HROOTMASS=next root mass in sequence

TAILMASSES=remaining masses

ACCUMSEQUENCE=current set of solutions

The $\dot{b}_j$ and $\dot{y}_j$ columns represent differences between adjacent masses. The differencing operation is referred to as differentiation and is the discrete data analogue of continuous data differentiation. In Table 3 the ordering has been reversed. The sequences have been obtained from the differentiated series. It can be seen that both series share the part sequence YLKGE (amino acids 2-6 of SEQ ID NO: 4).

The Reflective Predicate Filter works by only including those pairs of $m_{DN}$ that have a match between differentiated masses in reverse order. This property is represented mathematically as:

$$R_j \dot{m}_{DN} \text{ is a contiguous subsequence of } {}_k\dot{m}_{DN}$$

where ${}_j\dot{m}_{DN}$ denotes a vector of mass differences, or first differential of $m_{DN}$. R denotes a reversing diagonal matrix—for example for a 3×3 matrix it is:

$$\begin{array}{ccc} 0 & 0 & 1 \\ 0 & 1 & 0 \\ 1 & 0 & 0 \end{array}$$

This "contiguous subsequence property" requires the vector on the left hand side to be wholly contained within the vector on the right hand side and in the same order. For example the vector [1,2,3] is a contiguous subsequence of [7,8,1,2,3,5] and not a contiguous subsequence of [1,2] or [1,2,5,3]. If the property above is satisfied both ${}_jm_{DN}$ and ${}_km_{DN}$ are included in the filtered subset—the two series are known as reflective pairs.

Such reflected series are denoted by $m_R$. The normal subset condition holds:

$$\forall m_R \in m_{DN} \in M$$

i.e. each $m_R$ set is a subset of an $m_{DN}$ set, which in turn is a subset of M.

Table 4 shows the results of the Reflective Predicate Filter. The filter tends to fragment long series. Critically, it acts to eliminate false peaks as is demonstrated by the elimination of the false 538 mass peak from the a-18 series 11. The series now shown at column 11 of Table 4 is a contiguous subsequence of the series shown at column 11 of Table 1, and which was identified by the method of the present invention but not previously shown. Of the 15 series, 7 are correct whole or fragments of genuine series corresponding to SEQ ID NO: 1.

Neutral Loss Predicate

Subsequent to the filtering achieved by the Reflective Predicate Filter, an additional filtering method is employed to identify Displacement Ions. In this case it is the Neutral Loss Predicate, which is a deductive method. In other cases, or in addition to inductive predicates, inductive methods such as Supervised Machine Learning algorithms can be used to filter and/or classify the candidate m/z peak sets. The Neutral Loss Predicate works in a similar fashion to the Mass Difference Predicate described above, but is based upon the neutral losses which can occur with certain ion species. The exact nature of the neutral losses is determined by the nature of the ions themselves and the identification of a neutral loss species can therefore be used to determine information about the ion species. For example, certain amino acids will undergo certain neutral losses. Therefore, a given ion species having a neutral loss can be determined as containing a specific amino acid, or as comprising one of a set of amino acids. Since the neutral loss occurs from the terminus of an ion species it is also therefore possible to determine the location of a particular amino acid or of one of a set of amino acids responsible for the neutral loss.

Details of neutral losses which occur with amino acids are given in FIG. 3. Examples of neutral losses are 18 ($H_2O$), 17 ($NH_3$) and 34 ($H_2S$).

Once such neutral losses have been identified the candidate m/z peak sets can then be labelled as being neutral loss sets and, as appropriate, as having certain properties, i.e. putatively containing certain amino acids. In order to further simplify the candidate m/z peak sets, the neutral loss sets can be correlated with the candidate m/z peak sets containing the same ordered peaks, which can in turn be attributed any labels given to the mass peaks of one another, and the shortest candidate m/z peak set discarded.

As can be seen from Table 4, the candidate m/z peak sets remaining after the Reflective Predicate Filter contain members which have m/z values which are displaced from those in other sets by fixed amounts. For example, in column 6 of Table 4 the candidate m/z peak set has the members 959 and 846. They are displaced by 18 u from the 977 and 864 members of the candidate m/z peak set given at column 5 of Table 4, which has members with values 1076, 977, 864 and 777.

Thus this filtering mechanism works by selecting pairs of sets that have 2 or more peaks separated by known Displacement Masses. From the Difference Equations, it can be seen that: $b_j - a_j = 28$ As well as providing a filtering mechanism, the Mass Difference Predicates can also be used as a series classifier, as only a- and b-series are displaced by 28 Daltons. The classification into series type is discussed further below.

As well as a- and b-series, it is possible to have y- and x-series ions which are separated by 26 Daltons, although in practise x-series are rarely found. As is the case with the Reflective Predicate Filter, both series satisfying the Mass Difference Predicate are included into the filtered set. Such pairs of series are known as Displacement Pairs.

The Mass Difference Predicate also holds between b- and c-series—in this case the mass difference value is that of $NH_3$-17 Daltons. Similarly, y- and z-series ions are displaced by 17 Daltons.

All 28 Daltons mass difference series are represented as $m_{DN-28}$ and again the subset condition holds:

$$\forall m_{DN-28} \in m_{DN} \in M$$

In some instances the Mass Difference Predicates are applied to the subset of reflectively filtered series, and in this case:

$$\forall m_{DN-28} \in m_R \in m_{DN} \in M$$

With the remaining candidate m/z peak sets, an additional step is performed to remove those candidate m/z peak sets which are contiguous subsequences of others (i.e those whose members do not just form a subset of the members of another set or sets, but whose members form a contiguous subsequence of another set or sets).

The amino acid sequences represented by the candidate m/z peak sets can be determined by a simple look-up of the mass differences between the m/z peak values against a set of amino acid masses. Thus a set of m/z peak values can be readily translated into an amino acid sequence. This can be done starting from the heaviest m/z peak value or from the lightest or in any other order. However, the resultant sequence still needs to be assigned a directionality—the ion species from which the sequences are determined could be a, b, or c-ions which will give, going from the heaviest m/z peak value to the lightest, an amino acid sequence in the direction C to N. Alternatively, the ion species from which the sequences are determined could be x-, y-, or z-ions which will give, going from the heaviest m/z peak value to the lightest, an amino acid sequence in the direction N to C. Amino acid sequences are commonly represented in the N to C direction and sequence derived from a-, b- and c-ion species must not be confused with sequence derived from x-, y- and z-ion species.

Thus a step in the process of determining a putative amino acid sequence can be to determine the directionality of the amino acid sequences represented by the candidate m/z peak sets, and this can be done as discussed by Papayannopoulos, IA (supra). Essentially, since the precursor mass for the sample polypeptide has been determined, and the candidate m/z peak set values are known, the heaviest values in each of the sets can be compared with the precursor ion mass to identify any differences which correlate to the mass of an amino acid, or to the mass of an amino acid+18 u. If a candidate m/z peak set is found whose greatest m/z peak value is equal to the sample polypeptide precursor mass minus the mass of an amino acid then the candidate m/z peak set is a y-series whose C-terminal member is the amino acid corresponding to the mass difference. Alternatively, if a candidate m/z peak set is found whose greatest m/z peak value is equal to the sample polypeptide precursor mass minus 18 and minus the mass of an amino acid then the candidate m/z peak set is a b-series whose N-terminal member is the amino acid corresponding to the mass difference plus 18.

For example, in FIG. 2 two candidate m/z peak sets are shown corresponding to the sequences REGGAIFE (SEQ ID NO: 1) and EFIAGGER (SEQ ID NO: 16) but there is no indication of directionality—the above step allows a directionality to be assigned to candidate m/z peak sets.

b-y Series Classification (Classification Predicate)

In order to determine whether a candidate m/z peak set might be a b- or y-series, the following can be derived from the $b_j$ and $y_j$ equations:

$$[b_{n-1}] = \sum_{i=1}^{n-1} aa_i + [N - \text{term}] \quad \text{[Equation 1]}$$
$$= [\text{precursor ion} + H^+] - aa_n - 18$$

$$y_{n-1} = [\text{precursor} + H^+] - aa_2 \quad \text{[Equation 2]}$$

Thus the following is true:

$$b_n = [\text{precursor ion} + H^+] - 18 \quad \text{[Equation 3]}$$

When the conditions set out in Equations 1-3 are applied to the highest mass, a number of different scenarios can result namely:

1. The series is ambiguously classified as both y- and b-series;
2. The series is classified as a b-series and not as a y-series;
3. The series is classified as a y-series and not as a b-series; and
4. The series is not classified as either a b-series or y-series Possible b- and y-series are found as pairs satisfying the reflective predicate. To these pairs the classification of each series in the pair is attempted using the equations above. The 4 scenarios for each series in the pair gives 16 possible outcomes, which can be represented by a matrix. The decision made for classification can be made by using a logic based Karnaugh map as shows in FIG. 7.

With reference to FIG. 7, it can be seen that for example if Series1 is classified as a b-series and not as a y-series, but Series2 is ambiguously classified as both a b- and y-series then Series1 is classified as a b-series and Series2 as a y-series.

Of the 16 scenario conditions, 6 can result in a classification error. If a classification error results then Difference Series can be calculated for difference values of −28 (a-series), −45 (a-17 series) and −46 (a-18 series). The total number of a-series and their neutral loss displacements can be compared for Series1 and Series2 and whichever series has the most is classified as the b-series. This classification method relies on the assumption that a-series are common and x-series are rare.

Finding Neutral Loss and a-series from b- and y-series:

Further neutral loss series and a-series, together with a neutral loss series can be calculated for the already classified b- and y-series. Displacement values of −17, −18, −28, −45 and −46 are used to respectively compute b-17, b-18, a-, a-17 and a-18 Displacement Series from the classified b-series. Similarly displacement values of −17 and −18 are used to respectively compute y-17 and y-18 Displacement Series from the classified y-series. From the b- and y-series relationship with precursor mass, namely:

$$b_j + y_{n-j} = [\text{precursor ion}] + 1 \quad \text{[Equation 4]}$$

equations can be derived to compute a-series from y-series and y-17 series from b-series as follows:

$$a_j + y_{n-j} = [\text{precursor ion}] - 27 \quad \text{[Equation 5]}$$

$$b_j + y - 17_{n-j} = [\text{precursor ion}] - 16 \quad \text{[Equation 6]}$$

Similar equations involving y-series ion masses with b-17, b-18, a-17 and a-18 ion series masses and the precursor ion mass can be derived by replacing −27 in Equation 5 by respectively −16, −17, −44 and −45. A similar relationship involving the b-series ion masses with y−18 and the precursor ion mass can be derived by replacing −16 in Equation 6 with −17.

Using the two methods outlined above it is readily possible to determine Displacement Series from series from the same terminal end with a simple displacement factor and from the opposite end from a simple displacement factor together with the mass of the precursor ion. Thus it is possible to have two version of the same Displacement Series type, say a-18, calculated from either terminal end of the peptide. Namely an a-18 series represented by the two sets:

a-18$_{CTerm}$; and a-18$_{NTerm}$.

An attempt can then be made to combine the two sets, and if the combined set satisfies the Mass Difference Predicate then it can be used in place of each of the two sets. If it does not satisfy the Mass Difference Predicate then both series are separately reported.

Thus:

$$a\text{-}18_{combined} = a\text{-}18_{CTerm} + \cup a\text{-}18_{NTerm}$$

$$y_{n-1} = [\text{precursor} + H^+] - aa_2 \quad \text{[Equation 7]}$$

Given that the C-terminus is OH, the following is true:

$$y_1 = aa_n + [\text{C-term}] + [H] + [H^+] = aa_n + 19 \quad \text{[Equation 8]}$$

Scoring of m/z Peak Sets:

A score system for b- and y-series is calculated by summing the number of possible Displacement Masses for each series. All other series are given a score of 0. The possible Displacement Masses and offsets are shown in Table 7. The total number of Displacement Masses for each possible Displacement Series is divided by the number of masses in either the b- or the y-series (as appropriate), giving a value <=1. Table 7 shows the Displacement Series used for b- and y-series. The b-series have 5 possible Displacement Series giving a maximum displacement score of 5. The y-series have 2 possible Displacement Series and have a maximum score of 2.

For b-series, an additional scoring factor, based on classifying the highest mass in a series as either the highest mass or the second highest mass in a b-series, is calculated. For y-series, the highest mass is classified against only a y-series second highest mass, as the highest mass in a y-series is the same as that of the precursor ion mass. These top mass conditions are set out in Equations 1-3.

If the highest mass in a y-series does not meet this criteria then an attempt to classify the lowest mass in the series as a y$_1$ ion is made. The lowest mass in the y-series is classified as a y$_1$ ion if it meets the condition in Equation 10. If either of the criteria described is met for a b- or y-series then 1.0 is added to the displacement score, giving a composite score.

The logic for the score adjustment is shown in flow chart form in FIG. 6. In the chart of FIG. 6, 10 is equivalent to "Yes", 20 is "No". Other parts of the chart are as follows:

30: $b_{top}$=[Precursor ion+H$^+$]−18
40: $b_{top-1}$=[Precursor ion+H$^+$]−18−[amino mass]
50: $b_{adjusted\ score}$=Displacement Score
60: $b_{adjusted\ score}$=Displacement Score+1
70: $y_{top-1}$=[Precursor+H$^+$]−[amino mass]
80: $Y_{adjusted\ score}$=$b_{adjusted\ score}$+1
90: $y_{bottom}$=[amino mass]+19
100: $y_{adjusted\ score}$=$b_{adjusted\ score}$ $$y_j = [C\ \text{term}] + \sum_{i=(n-j+1)}^{n} aa_i + [H] + [H^+] \quad \text{[Equation 9]}$$

[C-term] is usually OH, and so y$_1$ can usually be derived as being:

$$y_1 = aa_1 + 19 \quad \text{[Equation 10]}$$

Determining Candidate m/z Peak Sets from (MS)$^n$ Data

As is discussed above, the present invention can be used with (MS)$_n$ data where n>2. FIG. 8 shows the multiple paths that can be obtained for a complex (ms)$^n$ tree data structure. All 4 paths shown share a common (ms)$^2$ spectrum, but each has a separate (ms)$^3$ spectrum. FIGS. 9-12 show how each of the 4 possible mass paths are resolved. The masses shown as dotted lines are not used in the construction of a compound (ms)$^n$ spectrum. Thus only a single precursor ion m/z peak is taken from an ms$^1$ spectrum. With subsequent (ms)$^n$ spectra, all peaks having an m/z value greater than or equal to the m/z value of the precursor ion used in any subsequent (ms)$^n$ spectrum. Thus if there are no further (ms)$^n$ spectra obtained, all peaks in the final spectrum are used. Each series of masses from the path is used as an input into the putative series predicate. Each of the putative series is then used as an input to other predicates in order to determine b-y pairs etc. The amino acid sequence, determined from each path may differ or may be identical. If the sequences are identical they are combined. Scoring can also be incorporated, and a composite score associated with the sequence. The composite score is calculated by summing the individual sequence scores determined as described above.

The determination of Difference Sets can be done as described above, or supervised learning algorithms can be used. As an example, Table 5 shows a part of a training data set passed to a supervised learning algorithm and which has just six m/z peaks labelled M1-M6. Table 6 shows examples of classification given to the m/z peaks—the "series" column denotes the actual type of series which is represented by the m/z peaks, and the "classification" column denotes the classification assigned to the series by the supervised learning algorithm.

Combining (Splicing) and Scoring Sequences

FIG. 2 demonstrates how sequences are determined, by subtracting adjacent series masses, in an ideal situation. It is possible to have a number of different scenarios when combining sequences from N- and C-terminal series. The different scenarios are demonstrated in FIG. 14 along with the mechanism used to combine (splice) the sequences. In FIG. 14, each circle represents a single amino acid in the sequence, such as G or A. Cross-hatched circles represent the longer series, and the solid circles represent the shorter series. Circles with cross-hatching and solid colouring represent parts of the long and short series that are common, i.e. the overlap segment.

In FIG. 14, 110, 140, 170, 210 and 250 represent long sequences. 120, 150, 180, 220 and 260 represent short sequences. 130 represents a single sequence resulting from splicing, namely long sequence 110. 160 represents a single extended sequence resulting from the splicing of sequences 140 and 150. 190 represents a first long sequence (Sequence1) resulting from the splicing of 170 and 180. 200 represents a second right-spliced sequence (Sequence2) resulting from the splicing of 170 and 180. 230 represents a first long sequence (Sequence1) resulting from the splicing of 210 and 220. 240 represents a second short sequence (Sequence2) resulting from the splicing of 210 and 220. 270 represents a first long sequence (Sequence1) resulting from the splicing of 250 and 260. 280 represents a second left-spliced sequence (Sequence2) resulting from the splicing of 250 and 260.

Each of the scenarios demonstrated (110-130, 140-160, 170-200, 210-240, and 250-180) has a region of overlap of 3 amino acids. The scenarios depicted as 110-130 and 140-160 are most common, where each of the long and short series are consistent with one another. For both of these cases a single series, which may be the longer series, or an extended version of the longer series, is generated. The single sequence deduced from each of the b- and y-series in FIG. 2 are represented by the scenario depicted as 140-160. 6 amino acids FIAGGE (amino acids 1-6 of SEQ ID NO: 3) are common.

The remaining scenarios (170-200, 210-240, and 250-180) show the mechanism used when the sequences are inconsistent with one another. For these scenarios, the longer of the two sequences is made one of the solution sequences. The other solution depends on whether an end section of the shorter sequence is an overlapping segment. The third scenario (170-200) has the right hand last 3 amino acids of the shorter sequence common with a middle part of the longer sequence. Sequence 2 is formed by taking the entire shorter sequence and adding the part of the longer sequence, after the overlap segment.

In the fourth scenario (210-240), the short sequence has differing mnemonics either side of the common segment, no attempt is made to combine the sequences, and the longer and shorter sequences become the 2 solutions. The fifth scenario (250-280) is similar to the third, but this time the common segment occurs on the left hand side of the shorter series.

The score value attributed to a sequence is based on the score value of the series from which it is deduced. For the first and second scenarios (110-130 and 140-160), which combine sequences, the score of the resulting single series is calculated by summing the individual series scores. For all of the other scenarios, Sequence 1 is given the score of the longer series and Sequence 2 that of the shorter.

With this information, at least one putative amino acid sequence has been determined for a sample polypeptide.

It will be appreciated that it is not intended to limit the invention to the above example only, many variations, such as might readily occur to one skilled in the art, being possible, without departing from the scope thereof as defined by the appended claims.

TABLE 1

| Series | Mass | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|---|
| y1 | 147 | y | y | | | | | | | | | | | | | y | | y | y | |
| LV-28 | 185 | | | | | | | | | | | | | | | | | | | |
| a2-18 | 197 | | | | a-18 | | | | | | | a-18 | | | | | | | a-18 | |
| Internal | 213 | | | | | | | | N | | | | | | | | | | | |
| a2 | 215 | | | | | | | | | | | | | | | | | | | |
| b2-18 | 225 | | | | | b-18 | | b-18 | | | | | b-18 | b-18 | | b-18 | | | | |
| b2 | 243 | | | | | | | | b | | | | | | | | | | | b |
| y2 | 262 | y | | | | | | | | y | | a-18 | a-18 | | y | | | y | | |
| a3-18 | 296 | | | | a-18 | a-18 | | | | | | a-18 | a-18 | | | | | | | |
| b3-18 | 324 | | | | | | | b-18 | | | | | | b-18 | | b-18 | | | | |
| y3 | 333 | y | y | | | | | | | | | | | | | | y | | | |
| b3 | 342 | | | | | | | | b | b | | | | | | | | | | b |
| a4-18 | 409 | | | | a-18 | a-18 | | | | | a-18 | a-18 | a-18 | | a-18 | | | | b | |
| b4-18 | 437 | | | | | | | | | | | | | | b-18 | | | | | |
| b4 | 455 | | | | | | | b | b | b | | | | | | b-18 | | | | |
| y4 | 462 | y | y | | | | | | | | | | | | | | | | | |
| --- | 489 | | | | | | | | | | | | | | | | N | N N | | N |
| --- | 506 | | | N | N | | | | | | | | | | | | | | | |
| b5-18 | 524 | | | | | | | | | | | | | | | b-18 | b-18 | | | |
| 2y10+2 | 538 | | | | | | | | | N | N | N | N | | | | | | | |
| b5 | 542 | | | | | | b | | b | b | | | | | | | | | | |
| y5 | 577 | y | y | y | | y | | | | | | | | | | | | | | |
| y6 | 664 | y | y | y | | y | | | | | y | | | | | | | | | |
| Precursor | 659 | | | | | | | | | | | | | | | | | | | |
| y7 | 777 | y | y | y | | y | | | | | | | | | | | | | | |
| y8-18 | 846 | y-18 | | | | | y-18 | | | | | | | | | | | | | |
| y8 | 864 | y | y | y | | y | | | | | | | | | | | | | | |
| y9-18 | 959 | | | | | | y-18 | | | | | | | | | | | | | |
| y9 | 977 | y | y | y | | | | | | | | | | | | | | | | |
| y10 | 1076 | y | y | y | y | y | | | | | | | | | | | | | | |

TABLE 2 b-series of LYLKGER (SEQ ID NO: 4)

| j | $b_j$ | $\dot{b}_j$ | $aa_j$ |
|---|---|---|---|
| 1 | 114 | — | — |
| 2 | 277 | 163 | Y |
| 3 | 390 | 113 | L |
| 4 | 518 | 128 | K |
| 5 | 575 | 57 | G |
| 6 | 704 | 129 | E |
| 7 | 860 | 156 | R |

TABLE 3 y-series of LYLKGER (SEQ ID NO: 4)

| j | $y_j$ | $\dot{y}_j$ | $aa_j$ |
|---|---|---|---|
| 7 | 878 | 113 | L |
| 6 | 765 | 163 | Y |
| 5 | 602 | 113 | L |
| 4 | 489 | 128 | K |
| 3 | 361 | 57 | G |
| 2 | 304 | 129 | E |
| 1 | 175 | — | — |

TABLE 4

Remaining candidate m/z peak sets after application of the Reflective Predicate Filter

| Series | Mass | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| y1 | 147 | y | | | | | | | | | | | | | | |
| LV-28 | 185 | | | | | | | | | | | | | | | |
| a2-18 | 197 | | | | | | | | | | | | a-18 | | | |
| Internal | 213 | | | | | | | | | | N | | | | | |
| a2 | 215 | | | | | | | | | | | | | | | |
| b2-18 | 225 | | | | | | | | b-18 | | | | | | | |
| b2 | 243 | | | | | | | | b | | | | | | | |
| y2 | 262 | y | y | | | | | | | | | | y | | y | |
| a3-18 | 296 | | | | | | | | a-18 | | | | a-18 | | a-18 | |
| b3-18 | 324 | | | | | | | | | | | | | | | |
| y3 | 333 | | y | y | | | | | | | | | | | | |
| b3 | 342 | | | | | | | | b | b | | | | | | |
| a4-18 | 409 | a-18 | | | | | | | | | | a-18 | a-18 | a-18 | a-18 | |
| b4-18 | 437 | | | | | | | | | | | | | | | |
| b4 | 455 | | | | | | | | b | | | | | | | |
| y4 | 462 | | y | y | | | | | | | | | | | | |
| - | 489 | | | | | | | | | N | | | | | | |
| - | 506 | | | | | | | | | | | | | | | N |
| b5-18 | 524 | | | | | | | | | | | | | | | |
| 2y10+2 | 538 | | | | | | | | | | | | | N | N | |
| b5 | 542 | | | | | | | | b | | | | | | | |
| y5 | 577 | | | | | y | | | | | | | | | | y |
| y6 | 664 | | | | | | | | | | | | | | | |
| Precursor | 659 | | | | | | | | | | | | | | | |
| y7 | 777 | | | | | y | | | | | | | | | | |
| y8-18 | 846 | | | | | | y-18 | y-18 | | | | | | | | |
| y8 | 864 | | | | | y | | | | | | | | | | |
| y9-18 | 959 | | | | | | y-18 | | | | | | | | | |
| y9 | 977 | | | | | y | y | | | | | | | | | |
| y10 | 1076 | | | | | y | y | | | | | | | | | |

TABLE 5 part of a set of training data

| Sequence | M1 | M2 | M3 | M4 | M5 | M6 | Ser | SEQ |
|---|---|---|---|---|---|---|---|---|
| YELQDPR | 175 | 272 | 387 | 515 | 628 | 757 | y | 5 |
| YELQDPR | 114 | 213 | 326 | 441 | 498 | 611 | b | 5 |
| IVLDGLY | 182 | 295 | 352 | 467 | 580 | 679 | y | 6 |
| IVLDGLY | 157 | 214 | 377 | 506 | 605 | 704 | b | 6 |
| RALPPLR | 175 | 288 | 385 | 482 | 595 | 666 | y | 7 |
| RALPPLR | 167 | 293 | 406 | 534 | 649 | 746 | b | 7 |
| RGYEVVR | 114 | 213 | 376 | 447 | 633 | 704 | b | 8 |

Column headed "Ser" denotes Series
Column headed "SEQ" denotes SEQ ID NO

TABLE 6 example results of Difference Set classification by supervised learning algorithm, the method being applicable to Difference Sets.

| Sequence | M1 | M2 | M3 | M4 | M5 | M6 | Ser | Cls | SEQ |
|---|---|---|---|---|---|---|---|---|---|
| IWIDGVR | 114 | 300 | 413 | 528 | 585 | 684 | b | b | 9 |
| IWIDGVR | 175 | 274 | 331 | 446 | 559 | 745 | y | y | 9 |
| MEGNDLK | 132 | 261 | 318 | 432 | 547 | 660 | b | y | 10 |
| MEGNDLK | 147 | 260 | 375 | 489 | 546 | 675 | y | y | 10 |
| LGELDGR | 114 | 171 | 300 | 413 | 528 | 585 | b | b | 11 |
| LGELDGR | 175 | 232 | 347 | 460 | 589 | 646 | y | b | 11 |
| HYARGVR | 138 | 301 | 372 | 528 | 585 | 684 | b | b | 12 |
| HYARGVR | 175 | 274 | 331 | 487 | 558 | 721 | y | y | 12 |
| IEGITAR | 114 | 243 | 300 | 413 | 514 | 585 | b | y | 13 |
| IEGITAR | 175 | 246 | 347 | 460 | 517 | 646 | y | y | 13 |
| NWARGVR | 115 | 301 | 372 | 528 | 585 | 684 | b | b | 14 |
| NWARGVR | 175 | 274 | 331 | 487 | 558 | 744 | y | y | 14 |
| NADINRR | 115 | 186 | 301 | 414 | 528 | 684 | b | y | 15 |
| NADINRR | 175 | 331 | 445 | 558 | 673 | 744 | y | y | 15 |

Column headed "Ser" denotes Series
Column headed "SEQ" denotes SEQ ID NO
Column headed "Cls" denotes classification of series by supervised learning algorithm

TABLE 7 scoring Displacement Series

| Main Series | Displacement Series | Displacement Mass |
|---|---|---|
| b | b-17 | −17 |
| b | b-18 | −18 |
| b | a | −28 |
| b | a-17 | −45 |
| b | a-18 | −46 |
| y | y-17 | −17 |
| y | y-18 | −18 |

The invention claimed is:

1. A system for determining at least one putative amino acid sequence for a sample polypeptide, said sample polypeptide being partially degraded, said system comprising:
   (a) a memory storing processor readable instructions; and
   (b) a processor arranged to read and execute instructions stored in said memory;
   wherein said processor readable instructions contain instructions to:
   (i) control the processor to store in said memory a set of m/z peaks obtained from a soft ionization mass spectrum of said sample polypeptide giving said set of m/z peaks of ion species obtained from said partially degraded sample polypeptide and determine from said set of m/z peaks a plurality of candidate m/z peak sets, each m/z peak in each candidate m/z peak set differing from its at least one neighbor by the mass of an amino acid residue;
   (ii) control the processor to store in said memory each candidate m/z peak set determined at step (i);
   for each candidate m/z peak set stored in said memory:
   determine an associated sequence of mass differences between each m/z peak in the set and its at least one neighbor; and
   determine an associated sequence of mass differences in reverse order;
   process the determined sequences of mass differences and determined sequences of mass differences in reverse order using a reflective predicate filter to determine a plurality of candidate m/z peak sets in which each m/z peak set has an associated sequence of mass differences in reverse order that forms at least part of the sequence of mass differences of another of said candidate m/z peak sets determined at step (i); and
   discard any candidate m/z peaks not in the determined plurality of candidate m/z peak sets;
   (iii) control the processor to:
   identify candidate m/z peak sets in which mass differences between each m/z peak and at least one peak in the candidate m/z peak set having a closest m/z value above and/or below the peak correspond to that of a daughter ion or an end ion cluster; and discard any identified candidate m/z peak sets from the plurality of candidate m/z peak sets;

(iv) control the processor to process the plurality of candidate m/z peak sets to:

identify any candidate m/z peak set which is a contiguous subsequence of another candidate m/z peak set; and discard the identified candidate m/z peak sets from the plurality of candidate m/z peak sets; and (v) control the processor to determine an amino acid sequence for each remaining candidate m/z peak set, each amino acid sequence being that of the amino acids which correspond to the mass differences between each m/z peak and its at least one neighbor, said at least one putative amino acid sequence of said sample polypeptide being made up of one or more of said determined amino acid sequences.

2. A computer program product for determining at least one putative amino acid sequence for a sample polypeptide, said sample polypeptide being partially degraded and a soft ionization mass spectrum of said sample polypeptide having been obtained giving a set of m/z peaks of ion species obtained from said partially degraded sample polypeptide, the computer program product comprising a non-transient computer usable medium having a computer readable program code, said computer readable program code comprising:

(i) program code for determining a plurality of candidate m/z peak sets, from said set of m/z peaks, each m/z peak in each candidate m/z peak set differing from its at least one neighbor by the mass of an amino acid residue;

(ii) program code for determining from each candidate m/z peak set determined at step (i) a sequence of mass differences between each m/z peak in the set and its at least one neighbor, and determining an associated sequence of mass differences in reverse order;

processing the determined sequences of mass differences and determined sequences of mass differences in reverse order using a reflective predicate filter to determine a plurality of candidate m/z peak sets in which each m/z peak set has an associated sequence of mass differences in reverse order that forms at least part of the sequence of mass differences of another of said candidate m/z peak sets determined at step (i); and discard any candidate m/z peak sets not in the determined plurality of candidate m/z peak sets;

(iv) program code for:

identifying candidate m/z peak sets in which mass differences between each m/z peak and at least one peak in the candidate m/z peak set having a closest m/z value above and/or below the peak correspond to that of a daughter ion or an end ion cluster; and discarding any candidate m/z peak sets from the plurality of candidate m/z peak sets;

(v) program code for:

processing the plurality of candidate m/z peak sets to identify any candidate m/z peak set which is a contiguous subsequence of another candidate m/z peak set; and discarding the identified candidate m/z peak sets from the plurality of candidate m/z peak sets; and (vi) program code for determining an amino acid sequence for each remaining candidate m/z peak set, each amino acid sequence being that of the amino acids which correspond to the mass differences between each m/z peak and its at least one neighbor, each putative amino acid sequence comprising an at least partial putative amino acid sequence of said sample polypeptide and outputting the results to the user in any desired tangible form, to allow said user to putatively identify the amino acid sequence for said sample polypeptide.

3. The computer program according to claim 2, wherein said program code for identifying candidate m/z peak sets in which mass differences between each m/z peak and at least one peak in the candidate m/z peak set having a closest m/z value above and/or below the peak correspond to that of a daughter ion or an end ion cluster is written in a Logic Programming language.

4. The system according to claim 1, wherein the memory stores machine instructions for identifying candidate m/z peak sets in which mass differences between each m/z peak and at least one peak in the candidate m/z peak set having a closest m/z value above and/or below the peak correspond to that of a daughter ion or an end ion cluster by:

(a) with said remaining candidate m/z peak sets, calculating the difference between the heaviest m/z value in each candidate m/z peak set and said precursor mass of said sample polypeptide;

(b) comparing the differences with the masses of amino acids and with the masses of amino acids+18 u; and (c) correlating the results of comparison step (b), a difference equal to the mass of an amino acid indicating a y-series Difference Set having the amino acid at its C-terminus, and a difference equal to the mass of an amino acid+18 u indicating a b-series Difference Set having the amino acid at its N-terminus.

5. The system according to claim 1, wherein the memory stores machine instructions for identifying any candidate m/z peak sets in (i) by:

(a) from the set of m/z peaks obtained from the soft ionization mass spectrum having x peaks, identifying every possible set of candidate m/z peaks having between 2 and x members;

(b) determining in each candidate m/z peak set the mass difference between each m/z peak and its at least one neighbor; and (c) discarding every candidate m/z peak set having any mass difference which is not equal to the mass of an amino acid.

6. The system according to claim 1, wherein said mass spectrum is a $(MS)^n$ spectrum, wherein n is at least 2.

7. The system according to claim 1, wherein the memory additionally stores machine instructions for determining the precursor mass of said sample polypeptide.

8. The system according to claim 1, wherein the memory additionally stores machine instructions for determining the directionality of said at least one remaining candidate m/z peak set.

9. A method for determining at least one putative amino acid sequence for a sample polypeptide with a computer program using (a) a memory storing processor readable instructions, and (b) a processor arranged to read and execute instructions stored in said memory, said sample polypeptide being partially degraded, said method comprising causing a suitably programmed computer comprising machine readable instructions to perform the steps of:

(i) obtaining a soft ionization mass spectrum of said partially degraded sample polypeptide giving a set of m/z peaks of ion species obtained from said partially degraded sample polypeptide and storing said set of m/z peaks in said memory using said processor;

(ii) with said set of m/z peaks obtained in step (i), using said processor in determining a plurality of candidate m/z peak sets, each m/z peak in each candidate m/z peak set differing from its at least one neighbor by the mass of an amino acid residue;

(iii) with each candidate m/z peak set determined at step (ii), using said processor in:

determining an associated sequence of mass differences between each m/z peak in the set and its at least one neighbor;

determining an associated sequence of mass differences in reverse order;

processing the determined sequences of mass differences and determined sequences of mass differences in reverse order using a reflective predicate filter to determine a plurality of candidate m/z peak sets in which each m/z peak set has an associated sequence of mass differences in reverse order that forms at least part of the sequence of mass differences of another of said candidate m/z peak sets determined at step (ii); and discarding any candidate m/z peak sets not in the determined plurality of candidate m/z peak sets;

(iv) controlling said processor to:

identify candidate m/z peak sets in which mass differences between each m/z peak and at least one peak in the candidate m/z peak set having a closest m/z value above and/or below the peak correspond to that of a daughter ion or an end ion cluster; and discard any candidate m/z peak sets from the plurality of candidate m/z peak sets;

(v) controlling said processor to process the plurality of candidate m/z peak sets to:

identify any candidate m/z peak set which is a contiguous subsequence of another candidate m/z peak set; and discard the identified candidate m/z peak sets from the plurality of candidate m/z peak sets;

(vi) determining a putative amino acid sequence for each remaining candidate m/z peak set, each amino acid sequence being that of the amino acids which correspond to the mass differences between each m/z peak and its at least one neighbor, each putative amino acid sequence comprising an at least partial putative amino acid sequence of said sample polypeptide and outputting the results to the user in any desired tangible form, to allow said user to putatively identify the amino acid sequence for said sample polypeptide.

10. The method according to claim 9, wherein identifying candidate m/z peak sets in which mass differences between each m/z peak and at least one peak in the candidate m/z peak set having a closest m/z value above and/or below the peak correspond to that of a daughter ion or an end ion cluster comprises:

(a) with said remaining candidate m/z peak sets, calculating the difference between the heaviest m/z value in each candidate m/z peak set and said precursor mass of said sample polypeptide;

(b) comparing the differences with the masses of amino acids and with the masses of amino acids+18 u; and (c) correlating the results of comparison step (b), a difference equal to the mass of an amino acid indicating a y-series Difference Set having the amino acid at its C-terminus, and a difference equal to the mass of an amino acid+18 u indicating a b-series Difference Set having the amino acid at its N-terminus.

11. The method according to claim 9, wherein said sample polypeptide is partially degraded using an enzyme selected from the group consisting of exopeptidases and endopeptidases.

12. The method according to claim 11, wherein said sample polypeptide is partially degraded using the endopeptidase trypsin.

13. The method according to claim 9, wherein said plurality of candidate m/z peak sets is identified by:

(a) from the set of m/z peaks obtained in step (i) having x peaks, identifying every possible set of candidate m/z peaks having between 2 and x members;

(b) determining in each candidate m/z peak set the mass difference between each m/z peak and its at least one neighbor; and (c) discarding every candidate m/z peak set having any mass difference which is not equal to the mass of an amino acid.

14. The method according to claim 9, wherein the amino acid masses with which the mass differences are compared comprising amino acid masses selected from the group consisting of:

chemically and post-translationally modified amino acids.

15. The method according to claim 9, wherein said mass spectrum being a $(MS)^n$ spectrum, wherein n is at least 2.

16. The method according to claim 9, wherein further comprising the step of determining the precursor mass of said sample polypeptide.

17. The method according to claim 9, further comprising the step of determining the directionality of said at least one remaining candidate m/z peak set.

18. The method according to claim 9, wherein said at least one determined putative amino acid for said sample polypeptide comprises at least two putative partial sequences of said sample polypeptide.

19. A system for determining at least one putative amino acid sequence for a sample polypeptide, said sample polypeptide being partially degraded, said system comprising a processor and a non-transitory computer-readable storage medium encoded with computer-executable instructions which, when executed by said processor, cause the processor to execute a method comprising the steps of:

(a) obtaining a set of m/z peaks from a soft ionization mass spectrum of said sample polypeptide (b) determining from said set of m/z peaks a plurality of candidate m/z peak sets, each m/z peak in each candidate m/z peak set differing from its adjacent m/z peaks by the mass of an amino acid residue;

(c) determining a sequence of mass differences associated with each of the plurality of candidate m/z peak sets based upon mass differences between each m/z peak in the set and its adjacent m/z peaks;

(d) filtering the plurality of candidate m/z peak sets by:

(i) for each candidate m/z peak set, analyzing the determined sequence of mass differences associated with the candidate ink peak set determined at step (c) using a reflective predicate filter and discarding the candidate m/z peak set if the sequence of mass differences associated with the candidate m/z peak set in reverse order does not form at least part of a sequence of mass differences of another of said candidate m/z peak sets determined at step (c);

(ii) identifying and discarding any candidate m/z peak sets in which a mass difference between a m/z peak of the candidate m/z peak set and an adjacent m/z peak of the candidate m/z peak set corresponds to that of a daughter ion or an end ion cluster;

(iii) identifying and discarding any candidate m/z peak set which is a contiguous subsequence of another candidate m/z peak set; and (e) determining an amino acid sequence for each remaining candidate m/z peak set that has not been discarded, each amino acid sequence being determined based upon the mass differences between adjacent m/z peaks in a respective candidate m/z peak set and the associated amino acid residues used to determine the candidate m/z peak set at step (b), wherein said at least one putative amino acid sequence of said sample polypeptide comprises one or more of said determined amino acid sequences.

20. A computer program product for determining at least one putative amino acid sequence for a sample polypeptide, said sample polypeptide being partially degraded, the computer program product comprising a non-transient computer usable medium having a computer readable program code, said computer readable program code comprising instructions arranged to cause a computer to:
(a) obtain a set of m/z peaks from a soft ionization mass spectrum of said sample polypeptide
(b) determine from said set of m/z peaks a plurality of candidate m/z peak sets, each m/z peak in each candidate m/z peak set differing from its adjacent m/z peaks by the mass of an amino acid residue;
(c) determine a sequence of mass differences associated with each of the plurality of candidate m/z peak sets based upon mass differences between each m/z peak in the set and its adjacent m/z peaks;
(d) filter the plurality of candidate m/z peak sets by:
(i) for each candidate m/z peak set, analyzing the determined sequence of mass differences associated with the candidate m/z peak set determined at step (c) using a reflective predicate filter and discarding the candidate m/z peak set if the sequence of mass differences associated with the candidate m/z peak set in reverse order does not form at least part of a sequence of mass differences of another of said candidate m/z peak sets determined at step (c);
(ii) identifying and discarding any candidate m/z peak sets in which a mass difference between a m/z peak of the candidate m/z peak set and an adjacent m/z peak of the candidate m/z peak set corresponds to that of a daughter ion or an end ion cluster;
(iii) identifying and discarding any candidate m/z peak set which is a contiguous subsequence of another candidate m/z peak set; and
(e) determine an amino acid sequence for each remaining candidate m/z peak set that has not been discarded, each amino acid sequence being determined based upon the mass differences between adjacent m/z peaks in a respective candidate m/z peak set and the associated amino acid residues used to determine the candidate m/z peak set at step (b), wherein said at least one putative amino acid sequence of said sample polypeptide comprises one or more of said determined amino acid sequences.

21. A method for causing a computer to determine at least one putative amino acid sequence for a sample polypeptide with a computer program using (a) a memory storing processor readable instructions, and (b) a processor arranged to read and execute instructions stored in said memory, said sample polypeptide being partially degraded, said method comprising causing a suitably programmed computer comprising machine readable instructions to perform the steps of:
(i) obtaining a soft ionization mass spectrum of said partially degraded sample polypeptide giving a set of m/z peaks of ion species obtained from said partially degraded sample polypeptide and storing said set of m/z peaks in said memory using said processor;
(ii) with said set of m/z peaks obtained in step (i), using said processor in determining a plurality of candidate m/z peak sets, each m/z peak in each candidate m/z peak set differing from its at least one neighbor by the mass of an amino acid residue;
(iii) with each candidate m/z peak set determined at step (ii), using said processor in:
determining an associated sequence of mass differences between each m/z peak in the set and its at least one neighbor;
determining an associated sequence of mass differences in reverse order;
processing the determined sequences of mass differences and determined sequences of mass differences in reverse order using a reflective predicate filter to determine a plurality of candidate m/z peak sets in which each m/z peak set has an associated sequence of mass differences in reverse order that forms at least part of the sequence of mass differences of another of said candidate m/z peak sets determined at step (ii); and
discarding any candidate m/z peak sets not in the determined plurality of candidate m/z peak sets;
(iv) controlling said processor to:
identify candidate m/z peak sets in which mass differences between each m/z peak and at least one peak in the candidate m/z peak set having a closest m/z value above and/or below the peak correspond to that of a daughter ion or an end ion cluster; and
discard any candidate m/z peak sets from the plurality of candidate m/z peak sets;
(v) controlling said processor to process the plurality of candidate m/z peak sets to:
identify any candidate m/z peak set which is a contiguous subsequence of another candidate m/z peak set; and
discard the identified candidate m/z peak sets from the plurality of candidate m/z peak sets;
(vi) determining a putative amino acid sequence for each remaining candidate m/z peak set, each amino acid sequence being that of the amino acids which correspond to the mass differences between each m/z peak and its at least one neighbor, each putative amino acid sequence comprising an at least partial putative amino acid sequence of said sample polypeptide and outputting the results to the user in any desired tangible form, to allow said user to putatively identify the amino acid sequence for said sample polypeptide.

* * * * *

UNITED STATES PATENT AND TRADEMARK OFFICE
CERTIFICATE OF CORRECTION

PATENT NO.         : 8,620,588 B2                                                                Page 1 of 1
APPLICATION NO.    : 10/515955
DATED              : December 31, 2013
INVENTOR(S)        : May et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 671 days.

Signed and Sealed this
Twenty-second Day of September, 2015

Michelle K. Lee
*Director of the United States Patent and Trademark Office*